United States Patent
Eliason et al.

(10) Patent No.: US 9,764,049 B2
(45) Date of Patent: Sep. 19, 2017

(54) RADIATION DELIVERY SYSTEM AND METHOD

(71) Applicant: Phoseon Technology, Inc., Hillsboro, OR (US)

(72) Inventors: Garth Eliason, Portland, OR (US); Doug Childers, Portland, OR (US); Ed Kiyoi, Tigard, OR (US)

(73) Assignee: Phoseon Technology, Inc., Hillsboro, OR (US)

( * ) Notice: Subject to any disclaimer, the term of this patent is extended or adjusted under 35 U.S.C. 154(b) by 0 days.

(21) Appl. No.: 14/965,739

(22) Filed: Dec. 10, 2015

(65) Prior Publication Data

US 2017/0165385 A1    Jun. 15, 2017

(51) Int. Cl.
*A61L 2/10*    (2006.01)
*F21V 8/00*    (2006.01)

(52) U.S. Cl.
CPC .............. *A61L 2/10* (2013.01); *G02B 6/0045* (2013.01); *G02B 6/0066* (2013.01)

(58) Field of Classification Search
USPC ..... 250/453.1, 455.11, 492.1, 208.1, 453.11, 250/239
See application file for complete search history.

(56) References Cited

U.S. PATENT DOCUMENTS

| | | |
|---|---|---|
| 5,029,252 A | 7/1991 | Ameseder |
| 5,044,734 A | 9/1991 | Sperl et al. |
| 5,120,499 A * | 6/1992 | Baron ................... A61L 12/026 250/455.11 |
| 5,225,172 A | 7/1993 | Meyler et al. |
| 7,348,572 B2 | 3/2008 | Shin |
| 7,498,065 B2 | 3/2009 | Siegel |
| 8,955,249 B2 | 2/2015 | Veres et al. |
| 9,116,266 B2 * | 8/2015 | Nakai .................. G02B 6/0031 |
| 9,406,227 B1 * | 8/2016 | Banuelos ............. G08G 1/0955 |
| 9,632,228 B2 * | 4/2017 | Teragawa ............ G02B 6/0033 |

(Continued)

FOREIGN PATENT DOCUMENTS

CN    104045125 A    9/2014

OTHER PUBLICATIONS

TOPAS 8007x10 Data Sheet, TOPAS Advanced Polymers, Available Online at http://www.topas.com/sites/default/files/TDS_8007x10_english%20units_1.pdf, Jan. 14, 2015, 1 page.

(Continued)

*Primary Examiner* — Phillip A Johnston
(74) *Attorney, Agent, or Firm* — McCoy Russell LLP

(57) ABSTRACT

A method of irradiating a work piece may include forming a cutout recessed from a surface of a light guide, positioning the work piece inside the cutout, irradiating a light input surface of the light guide with UV light, and guiding the UV light from within the light guide through recessed surfaces of the cutout to irradiate the work piece. In this way more uniform irradiation of all curable surfaces of a work piece may be achieved, the energy and time consumed during irradiation of the work piece may be reduced thereby lowering operating costs, and the radiation delivery system may be made more compactly, thereby making it more convenient and practical for daily applications.

20 Claims, 12 Drawing Sheets

(56) References Cited

U.S. PATENT DOCUMENTS

2007/0206377 A1* 9/2007 Borup ............... A45C 11/005
362/156
2011/0085943 A1 4/2011 Barea

OTHER PUBLICATIONS

ISA Korean Intellectual Property Office, International Search Report and Written Opinion Issued in Application No. PCT/US2016/065431, dated Mar. 13, 2017, WIPO, 12 pages.

* cited by examiner

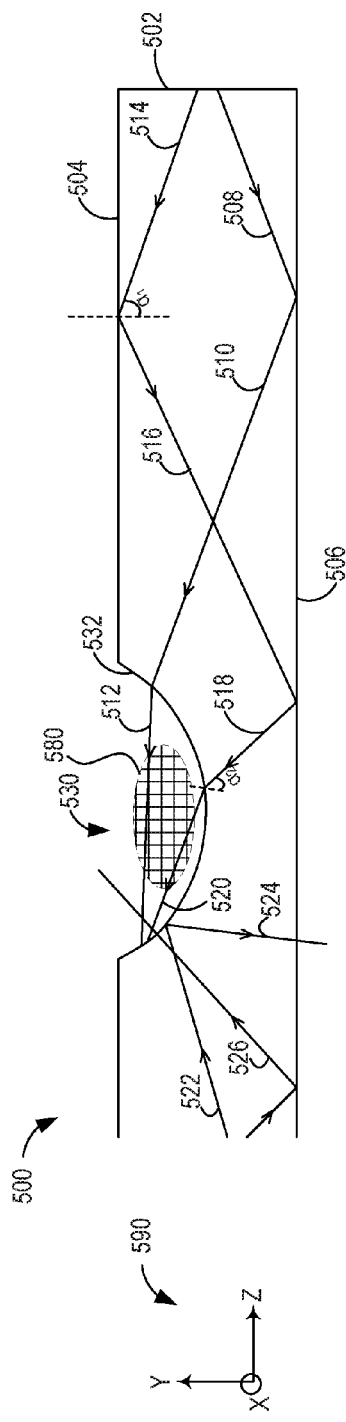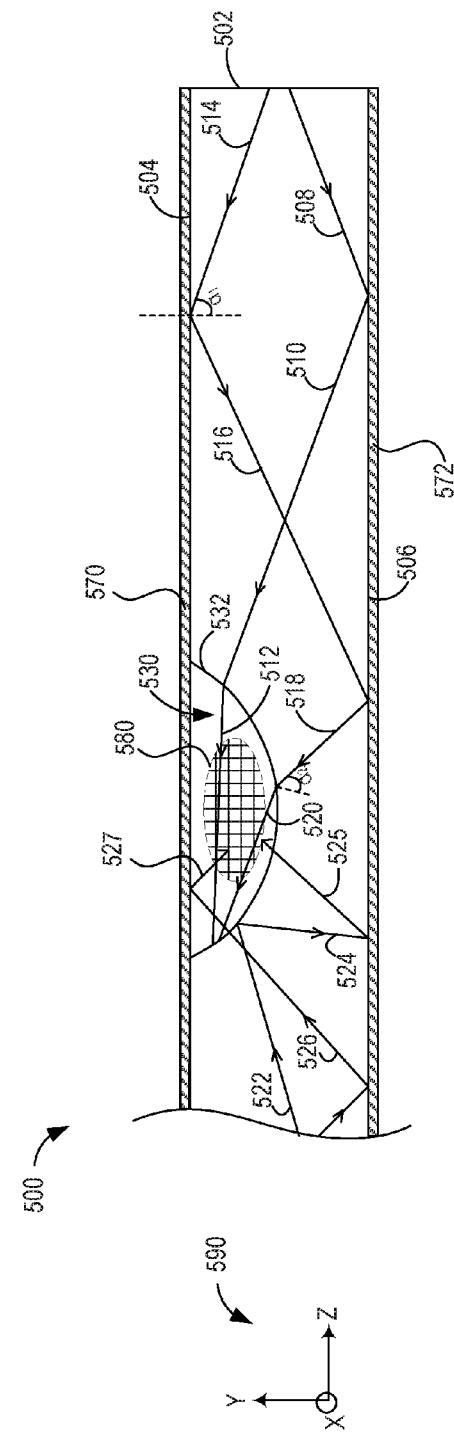

RADIATION DELIVERY SYSTEM AND METHOD

BACKGROUND AND SUMMARY

Disease-causing germs can live on many surfaces and therefore can be a vector for the spread of disease. Ultraviolet (UV) light is used for various applications such as disinfection and sterilization. Exposure to UV light kills or inactivates microorganisms, thereby rendering the microorganism incapable of reproducing and infecting. As an example, prior to surgery, surgical instruments may be exposed to UV light to disinfect and sterilize the instruments, thereby reducing any risk of exposing patients to unwanted surface microorganisms. Conventional UV sterilization technology includes large reflective chambers and gas lamp-based systems employing xenon and/or rare earth gases.

The inventor herein has recognized several issues with the above approaches. First, large reflective chambers and larger gas lamp-based systems are expensive and cumbersome, and not practical for daily use. Furthermore, more compact versions of gas lamp-based systems require larger voltage-driven power supplies to operate, are environmentally hazardous, and still remain large and unwieldy for a clinical or surgical setting. Further still, the UV illumination in such large chambers and gas lamp-based systems may not be uniform, which prolongs sterilization times and energy consumption, and increases operating costs.

One approach that at least partially addresses the above issues includes a method of irradiating a work piece comprising, forming a cutout recessed from a surface of a light guide, positioning the work piece inside the cutout, irradiating a light input surface of the light guide with UV light, and guiding the UV light from within the light guide through recessed surfaces of the cutout to irradiate the work piece.

In another example, a radiation delivery system may include a light guide comprising a UV transparent tray with one or more cutouts recessed from a surface of the tray, the one or more cutouts shaped to cradle one or more work pieces; and an array of light emitting elements arranged to direct radiation into a light input surface of the tray, wherein the one or more work pieces are irradiated by radiation transmitted from within the tray through recessed surfaces of the one or more cutouts.

In another example, a UV light guide for irradiating one or more work pieces, may comprise: one or more cutouts recessed from a surface of the UV light guide, the one or more cutouts shaped to cradle the one or more work pieces, wherein recessed surfaces of the one or more cutouts comprise UV transmissive surfaces for transmitting UV light from within the UV light guide on to the one or more work pieces.

In this way, the technical effect of delivering more uniform irradiation to the surfaces of a work piece may be achieved. Furthermore, the energy and time consumed during irradiation of the work piece may be reduced, thereby lowering operating costs. Further still, the radiation delivery system may be more compact, thereby making it more convenient and practical for daily applications.

It will be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 5A-5B are schematics illustrating UV rays being guided in a light guide, such as the light guides of FIGS. 2-4, from a light input surface through recessed surfaces of the light guide.

DETAILED DESCRIPTION

Figure 1:
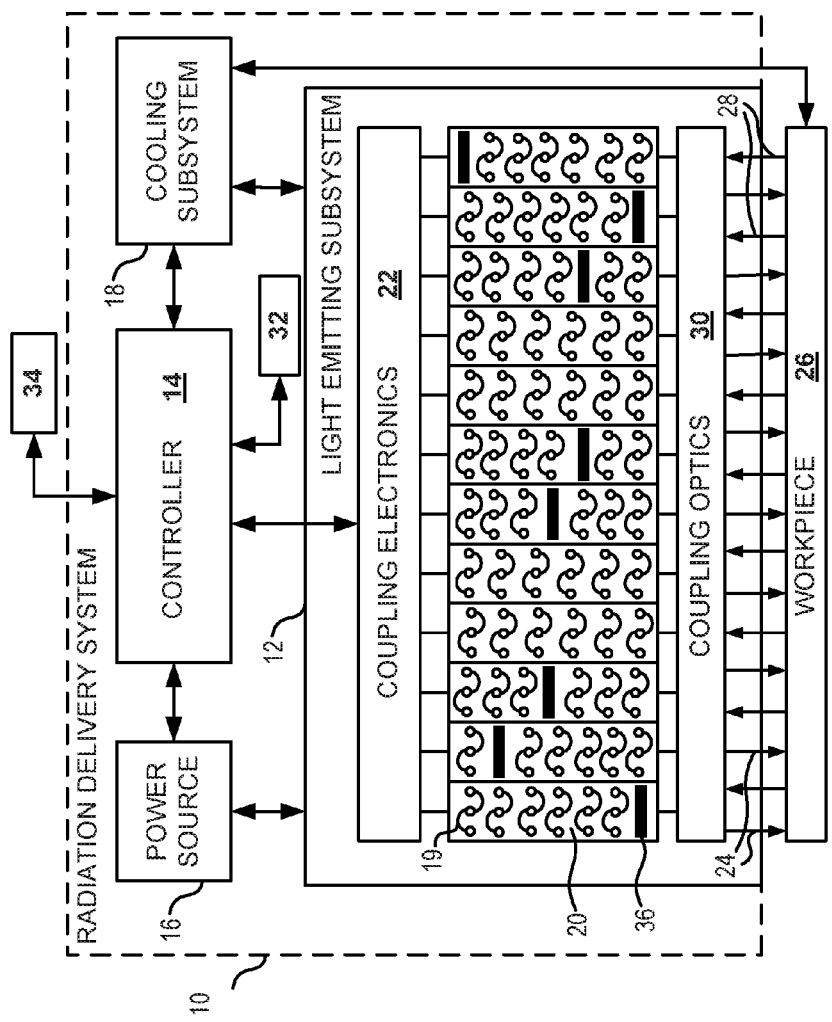
FIG. 1 illustrates an example of a radiation delivery system.
Figure 2:
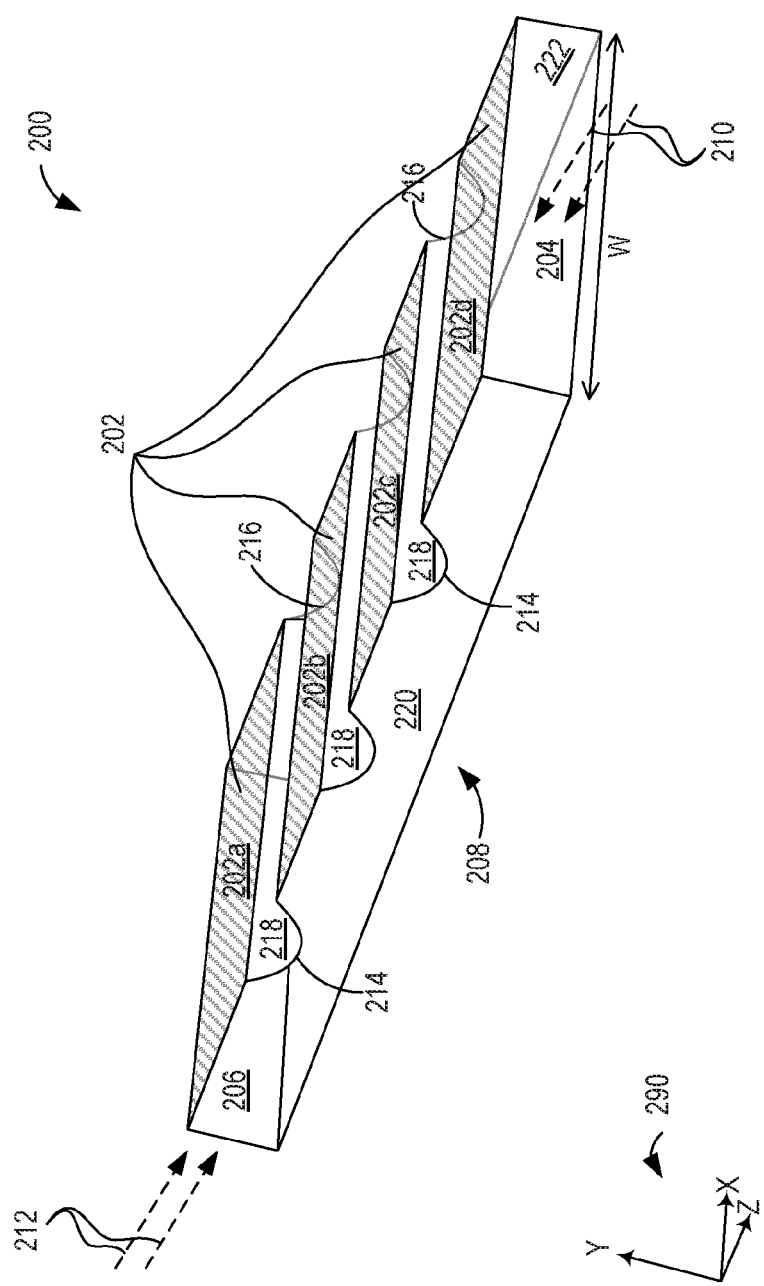
FIGS. 2-4 are perspective views of example light guides, each light guide including a recessed cutout and a light input surface.
Figure 3:
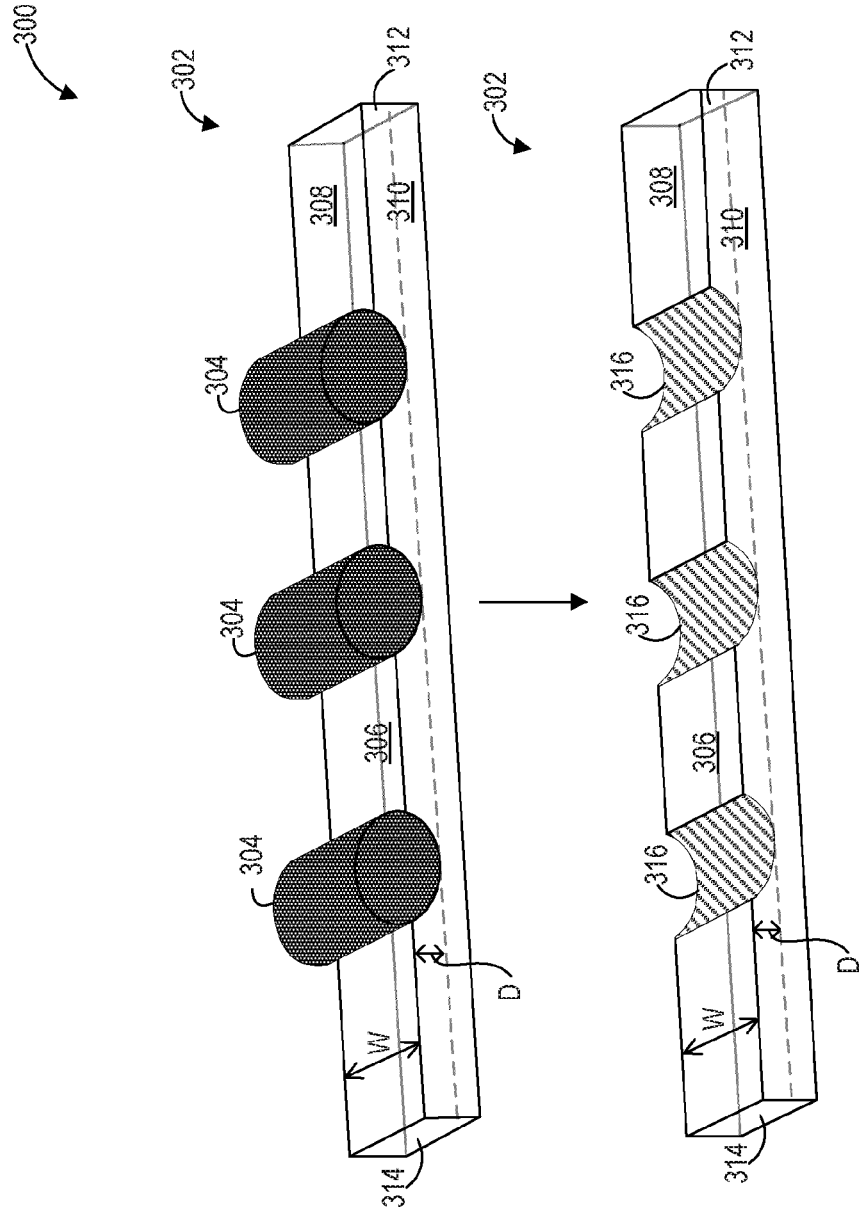
Figure 4:
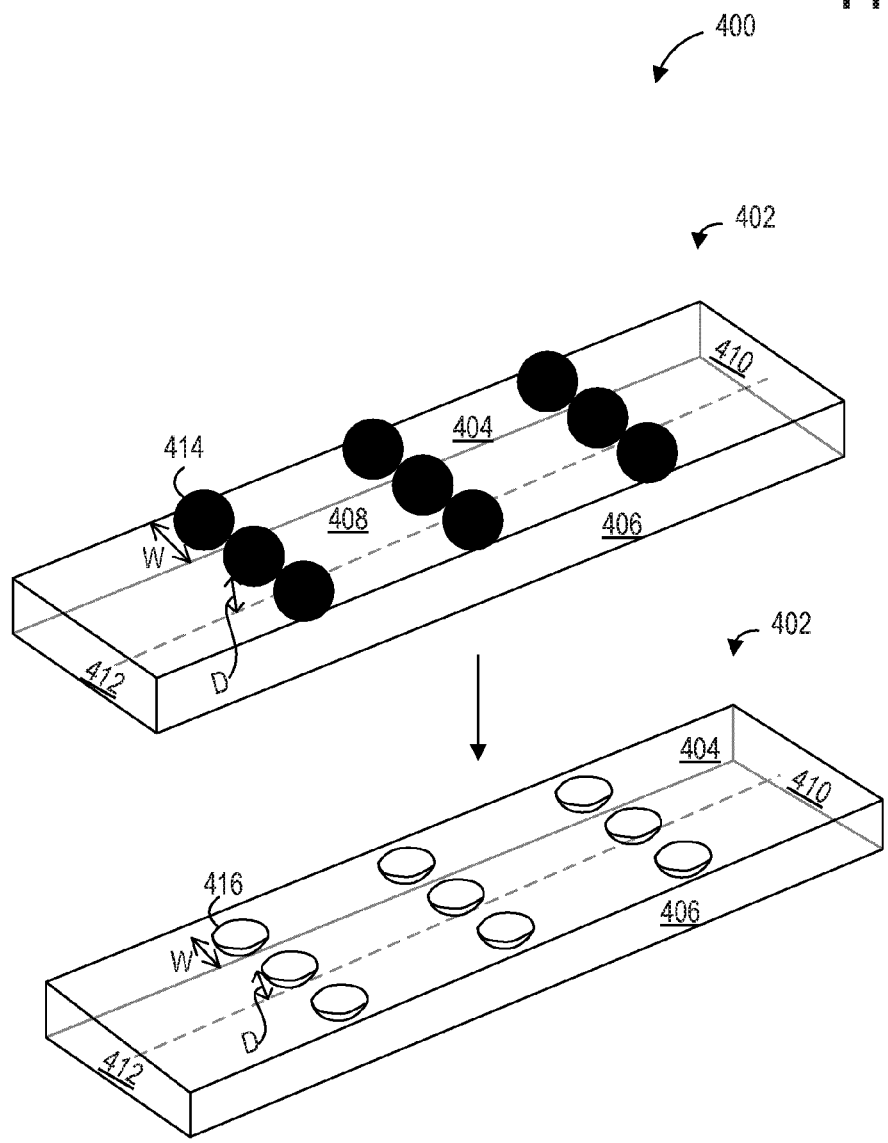
Figure 6:
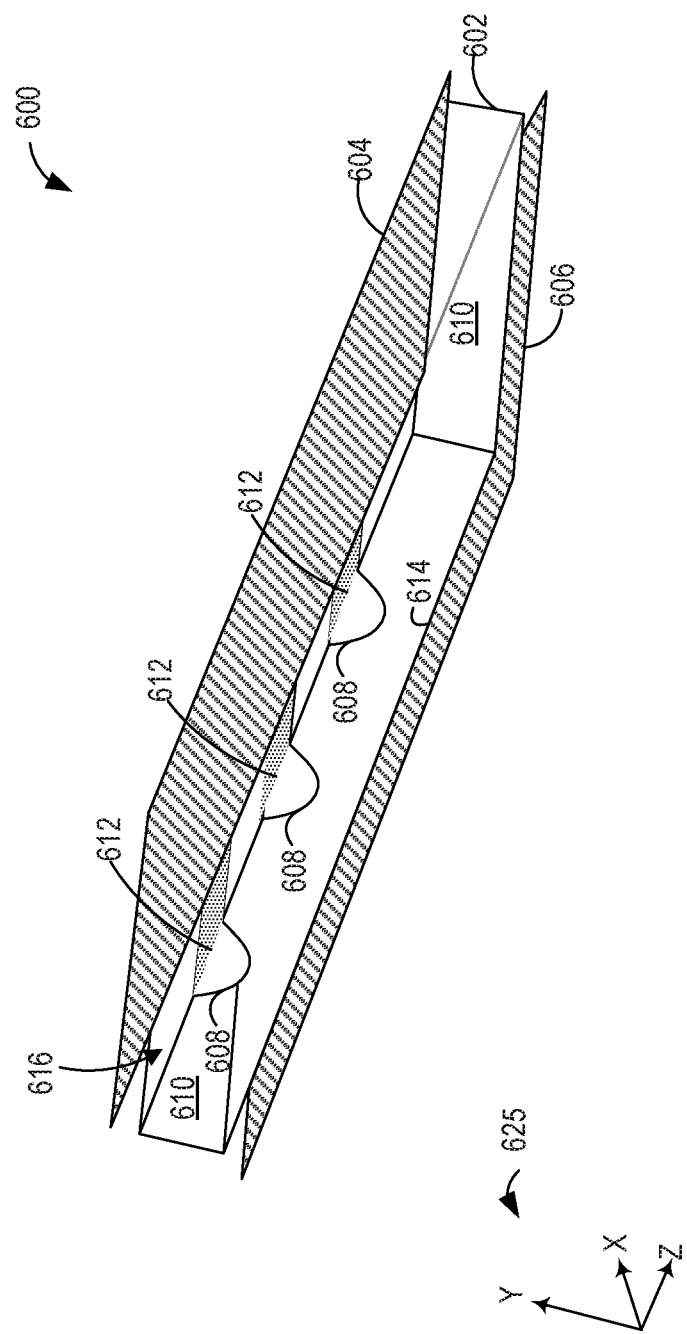
FIG. 6 illustrates an example light guide comprising a tray and UV reflective surfaces facing opposing parallel surfaces of the light guide.
Figure 7:
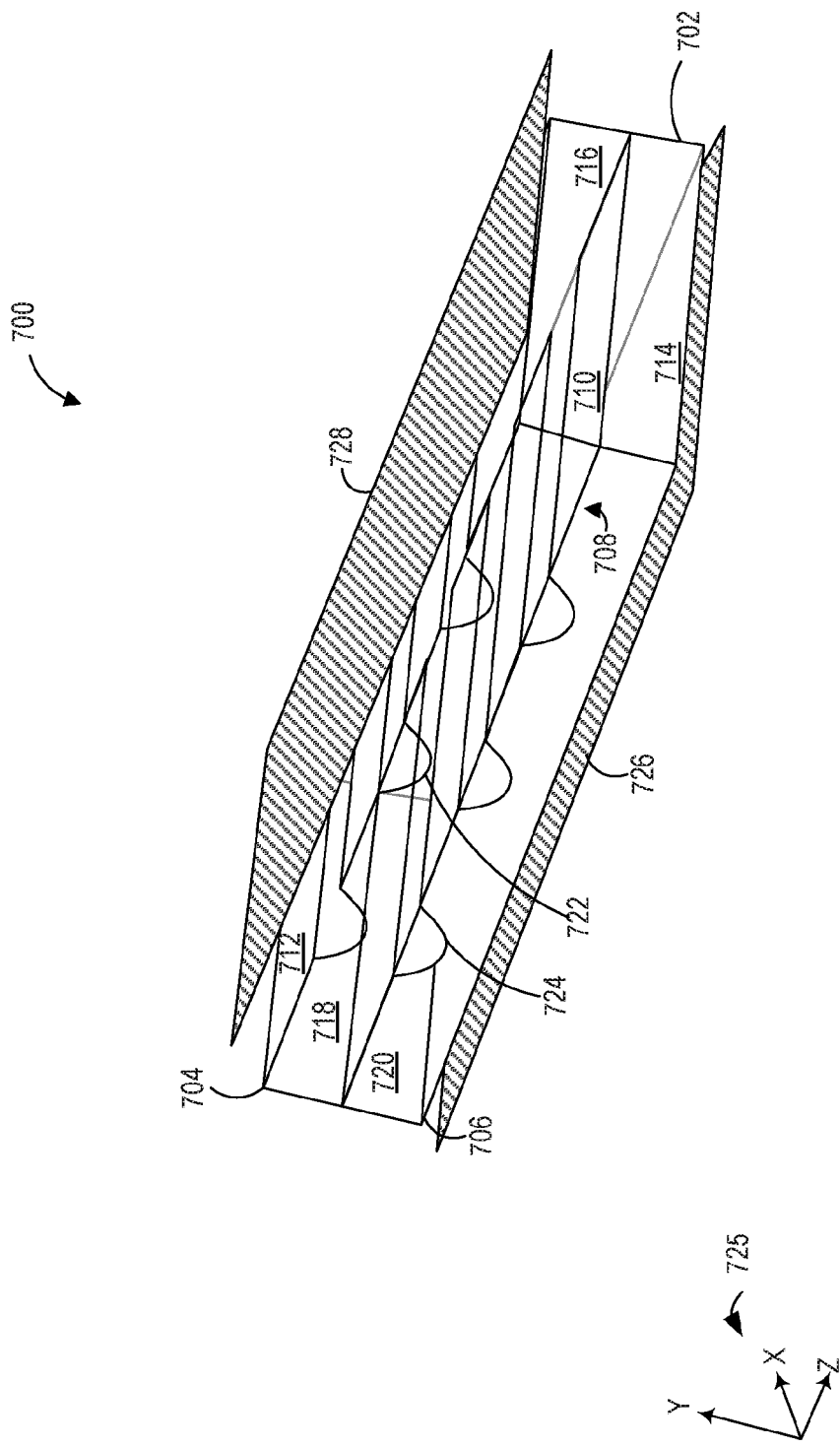
FIG. 7 illustrates an example light guide comprising a plurality of trays and UV reflective surfaces facing opposing parallel surfaces of the light guide.

The present description relates to methods and systems for irradiating a work piece with radiation, such as UV radiation. FIG. 1 illustrates an example of a radiation delivery system. Perspective views of example light guides are shown in FIGS. 2-4, where each light guide may include a recessed cutout and a light input surface. Some example geometries of different light guides including various recessed cutouts are shown in FIGS. 10A-10E. In some example embodiments, the light guide may include embedded cutouts as shown in FIGS. 11A-11E. Radiation may be guided by the light guides (such as the light guides of FIGS. 2-4) via total internal reflection (FIG. 9) and may illuminate from a light input surface through recessed surfaces of the light guide as shown in FIGS. 5A-5B. An example light guide comprising a tray and reflective surfaces facing opposing parallel surfaces of the light guide is shown in FIG. 6. An example light guide comprising a plurality of trays and reflective surfaces facing opposing parallel surfaces of the light guide is shown in FIG. 7. A controller may be configured to perform a routine, such as the routine of FIG. 8 to irradiate work pieces with a radiation delivery system including a light guide. Perspective views of example cabinets including multiple light guides with one or more cutouts, and radiation delivery systems positioned to direct light into the light guides are shown in FIGS. 12A-B.

Referring now to FIG. 1, it illustrates a block diagram for an example configuration of a radiation delivery system 10. For example, radiation delivery system 10 may include a lighting device, a curing system, a sterilization system, and the like. Radiation delivery system 10 may be used to emit radiation such as optical light, UV light, infrared light, and/or other types of radiation. In one example, radiation delivery system 10 may comprise a light-emitting subsystem 12, a controller 14, a power source 16 and a cooling subsystem 18. The light-emitting subsystem 12 may comprise a plurality of semiconductor devices 19. The plurality of semiconductor devices 19 may be an array 20 of light-emitting elements such as a linear array of LED devices, for example. Array 20 of light-emitting elements may also comprise a two-dimensional array of LED devices, or an array of LED arrays, for example. Semiconductor devices may provide radiant output 24. In one example, the radiant output 24 includes UV radiation. The radiant output 24 may be directed to a work piece 26 located at a fixed plane from radiation delivery system 10. Returned radiation 28 may be directed back to the light-emitting subsystem 12 from the work piece 26 (e.g., via reflection of the radiant output 24).

The radiant output 24 may be directed to the work piece 26 via coupling optics 30. The coupling optics 30, if used, may be variously implemented. As an example, the coupling optics may include one or more layers, materials or other structures interposed between the semiconductor devices 19 and work piece 26, and providing radiant output 24 to surfaces of the work piece 26. As an example, the coupling optics 30 may include a micro-lens array to enhance collection, condensing, collimation or otherwise the quality or effective quantity of the radiant output 24. As another example, the coupling optics 30 may include a micro-reflector array. In employing such a micro-reflector array, each semiconductor device providing radiant output 24 may be disposed in a respective micro-reflector, on a one-to-one basis. As another example, an array of semiconductor devices 20 providing radiant output 24 may be disposed in macro-reflectors, on a many-to-one basis. In this manner, coupling optics 30 may include both micro-reflector arrays, wherein each semiconductor device is disposed on a one-to-one basis in a respective micro-reflector, and macro-reflectors wherein the quantity and/or quality of the radiant output 24 from the semiconductor devices is further enhanced by macro-reflectors. For example, macro-reflectors may comprise elliptic cylindrical reflectors, parabolic reflectors, dual elliptic cylindrical reflectors, and the like.

In another example, coupling optics 30 may include a light guide, such as the light guide 200 shown in FIG. 2. A light guide may include a device designed to facilitate transmission of light from a light source to a work piece with minimal losses in the light intensity or irradiance. Light may be transmitted through a light guide by means including total internal reflection. Light guides may be manufactured from optical grade materials such as acrylic resin, polycarbonate, epoxies, glass, and the like. UV light guides may be manufactured from UV transparent materials such as fused silica, fused quartz, or other glass materials.

Figure 9:
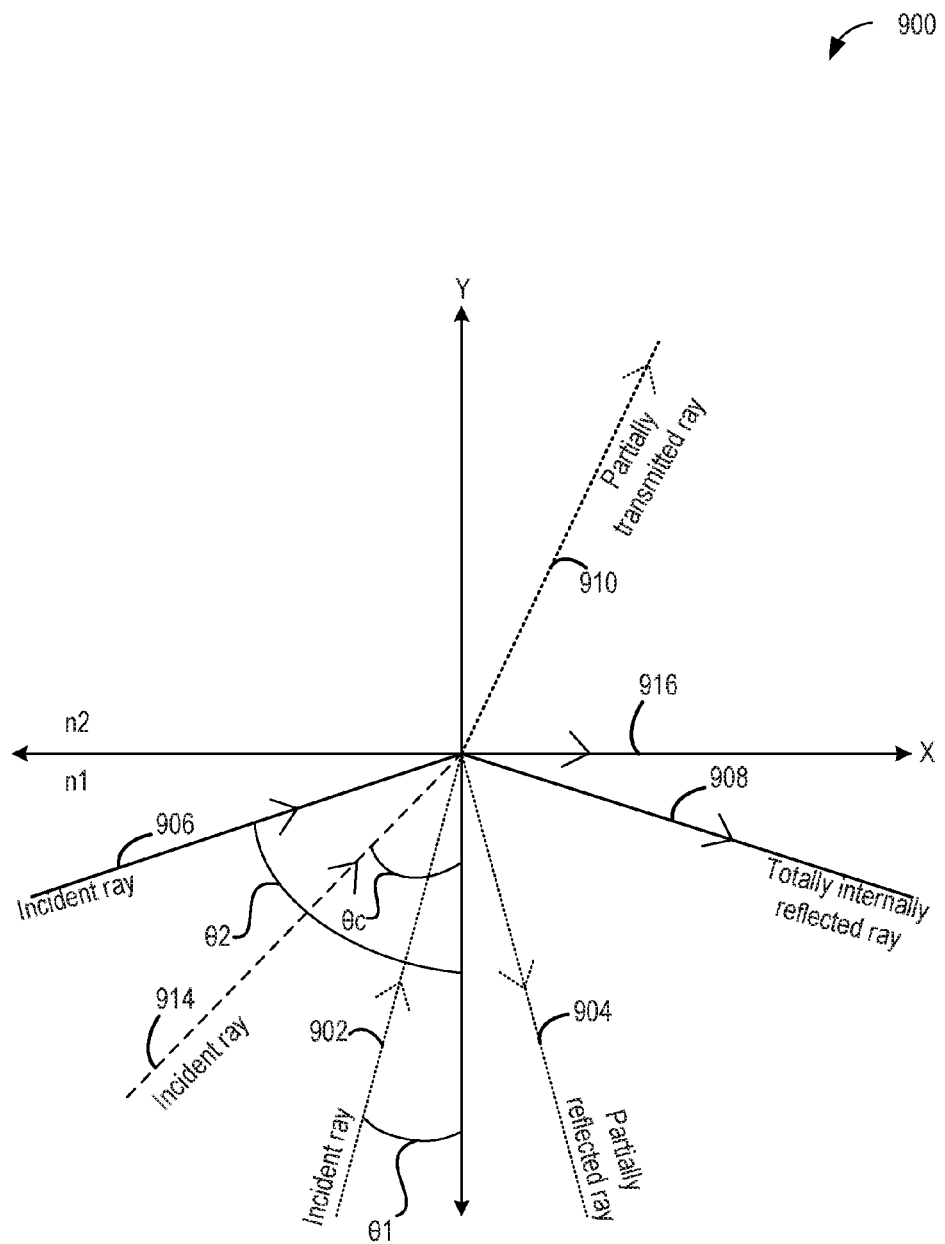
FIG. 9 illustrates an example ray diagram illustrating the principle of total internal reflection.

Total internal reflection, as shown in FIG. 9, is a phenomenon which occurs when a light strikes a surface at an angle larger than a particular critical angle ($\theta c$) with respect to the normal to the surface. Turning to FIG. 9, plot 900 shows the working principal of total internal reflection phenomenon. In plot 900, an incident ray of light 902 is incident at an angle $\theta 1$ at a boundary separating two media, one medium of refractive index n1 and the second medium with refractive index n2. The incident ray 902 may be partially reflected (904) and partially transmitted (910). An incident ray 906 is incident at an angle $\theta 2$ at the boundary separating the two media of refractive indices n1 and n2, where n2<n1. If the incident angle $\theta 2$ is greater than the critical angle $\theta c$, the incident ray 906 may be entirely reflected (908), or total internally reflected. For example, incident ray 914 incident at the boundary separating the two media at the critical angle $\theta c$ may be reflected along the interface of the boundary (916). The critical angle $\theta c$ is the angle of incidence above which the total internal reflection occurs. This can only occur when the radiation in a medium with a higher refractive index (n1) reaches a boundary with a medium of lower refractive index (n2). For example, it will occur with light reaching air from glass, but not when reaching glass from air. For glass material with refractive index n1=1.5, and when light travels from glass to air (n2=1), the critical angle may be calculated as 42°, for example. Thus, light incident at angles higher than 42° will be totally reflected back into the glass material.

Returning to FIG. 1, each of the layers, materials or other structure of coupling optics 30 may have a selected index of refraction. By properly selecting each index of refraction, reflection at interfaces between layers, materials and other structures in the path of the radiant output 24 (and/or returned radiation 28) may be selectively controlled. As an example, by controlling differences in such indexes of refraction at a selected interface, for example recessed surface of cutout 218 of light guide 200 shown in FIG. 2, disposed between the semiconductor devices and the work piece 26, reflection at that interface may be reduced or increased so as to enhance the transmission of radiant output at that interface for ultimate delivery to the work piece 26. For example, the coupling optics may include a light guide that guides UV light via total internal reflection from a light input surface to a recessed surface of a cutout, through which UV light is transmitted to a work piece. In another example the coupling optics may include a dichroic reflector where certain wavelengths of incident light are absorbed, while others are reflected and focused to the surface of work piece 26.

The coupling optics 30 may be employed for various purposes. Example purposes include, among others, to protect the semiconductor devices 19, to retain cooling fluid associated with the cooling subsystem 18, to collect, condense and/or collimate the radiant output 24, to collect, direct or reject returned radiation 28, or for other purposes, alone or in combination. As a further example, the radiation delivery system 10 may employ coupling optics 30 so as to enhance the effective quality, uniformity, or quantity of the radiant output 24, particularly as delivered to the work piece 26.

Selected of the plurality of semiconductor devices 19 may be coupled to the controller 14 via coupling electronics 22, so as to provide data to the controller 14. As described further below, the controller 14 may also be implemented to control such data-providing semiconductor devices, e.g., via the coupling electronics 22. The controller 14 may be connected to, and may be implemented to control, the power source 16, and the cooling subsystem 18. For example, the controller may supply a larger drive current to light-emitting elements distributed in the middle portion of array 20 and a smaller drive current to light-emitting elements distributed in the end portions of array 20 in order to increase the useable area of light irradiated at work piece 26. Moreover, the controller 14 may receive data from power source 16 and cooling subsystem 18. In one example, the irradiance at one or more locations at the work piece 26 surface may be detected by sensors and transmitted to controller 14 in a feedback control scheme. In a further example, controller 14 may communicate with a controller of another lighting system (not shown in FIG. 1) to coordinate control of both lighting systems. For example, controllers 14 of multiple lighting systems may operate in a master-slave cascading control algorithm, where the setpoint of one of the controllers is set by the output of the other controller. Other control strategies for operation of radiation delivery system 10 in conjunction with another lighting system may also be used. As another example, controllers 14 for multiple lighting systems arranged side by side may control lighting systems in an identical manner for increasing uniformity of irradiated light across multiple lighting systems.

In addition to the power source 16, cooling subsystem 18, and light-emitting subsystem 12, the controller 14 may also be connected to, and implemented to control internal element 32, and external element 34. Internal element 32, as shown, may be internal to the radiation delivery system 10, while external element 34, as shown, may be external to the radiation delivery system 10, but may be associated with the work piece 26 (e.g., handling, cooling or other external equipment) or may be otherwise related to a photoreaction (e.g. curing) that radiation delivery system 10 supports.

The data received by the controller 14 from one or more of the power source 16, the cooling subsystem 18, the light-emitting subsystem 12, and/or elements 32 and 34, may be of various types. As an example the data may be representative of one or more characteristics associated with coupled semiconductor devices 19. As another example, the data may be representative of one or more characteristics associated with the respective light-emitting subsystem 12, power source 16, cooling subsystem 18, internal element 32, and external element 34 providing the data. As still another example, the data may be representative of one or more characteristics associated with the work piece 26 (e.g., representative of the radiant output energy or spectral component(s) directed to the work piece). Moreover, the data may be representative of some combination of these characteristics.

The controller 14, in receipt of any such data, may be implemented to respond to that data. For example, responsive to such data from any such component, the controller 14 may be implemented to control one or more of the power source 16, cooling subsystem 18, light-emitting subsystem 12 (including one or more such coupled semiconductor devices), and/or the elements 32 and 34. As an example, responsive to data from the light-emitting subsystem indicating that the light energy is insufficient at one or more points associated with the work piece, the controller 14 may be implemented to either (a) increase the power source's supply of power to one or more of the semiconductor devices, (b) increase cooling of the light-emitting subsystem via the cooling subsystem 18 (e.g., certain light-emitting devices, if cooled, provide greater radiant output), (c) increase the time during which the power is supplied to such devices, or (d) a combination of the above. In this way, the controller 14 may be capable of regulating an intensity or exposure duration of radiant output 24 in response to a measured characteristic (e.g., irradiance, temperature, degree of cure, and the like) at one or more locations at the work piece 26 surface detected and/or measured by one or more sensors.

Individual semiconductor devices 19 (e.g., LED devices) of the light-emitting subsystem 12 may be controlled independently by controller 14. For example, controller 14 may control a first group of one or more individual LED devices to emit light of a first intensity, wavelength, and the like, while controlling a second group of one or more individual LED devices to emit light of a different intensity, wavelength, and the like. The first group of one or more individual LED devices may be within the same array 20 of semiconductor devices, or may be from more than one array of semiconductor devices 20 from multiple light-emitting subsystems 12. Array 20 of semiconductor device may also be controlled independently by controller 14 from other arrays of semiconductor devices in other lighting systems. For example, the semiconductor devices of a first array may be controlled to emit light of a first intensity, wavelength, and the like, while those of a second array in another curing device may be controlled to emit light of a second intensity, wavelength, and the like.

As a further example, under a first set of conditions (e.g. for a specific work piece, photoreaction, and/or set of operating conditions) controller 14 may operate radiation delivery system 10 to implement a first control strategy, whereas under a second set of conditions (e.g. for a specific work piece, photoreaction, and/or set of operating conditions) controller 14 may operate radiation delivery system 10 to implement a second control strategy. As described above, the first control strategy may include operating a first group of one or more individual semiconductor devices (e.g., LED devices) to emit light of a first intensity, wavelength, and the like, while the second control strategy may include operating a second group of one or more individual LED devices to emit light of a second intensity, wavelength, and the like. The first group of LED devices may be the same group of LED devices as the second group, and may span one or more arrays of LED devices, or may be a different group of LED devices from the second group, but the different group of LED devices may include a subset of one or more LED devices from the second group.

The cooling subsystem 18 may be implemented to manage the thermal behavior of the light-emitting subsystem 12. For example, the cooling subsystem 18 may provide for cooling of light-emitting subsystem 12, and more specifically, the semiconductor devices 19. The cooling subsystem 18 may also be implemented to cool the work piece 26 and/or the space between the work piece 26 and the radiation delivery system 10 (e.g., the light-emitting subsystem 12). For example, cooling subsystem 18 may comprise an air or other fluid (e.g., water) cooling system. Cooling subsystem 18 may also include cooling elements such as cooling fins attached to the semiconductor devices 19, or array 20 thereof, or to the coupling optics 30. For example, cooling subsystem may include blowing cooling air over the coupling optics 30, wherein the coupling optics 30 are equipped with external fins to enhance heat transfer.

The radiation delivery system 10 may be used for various applications. Examples include, without limitation, curing applications ranging from ink printing to the fabrication of DVDs and lithography. The applications in which the radiation delivery system 10 may be employed can have associated operating parameters. That is, an application may have associated operating parameters as follows: provision of one or more levels of radiant power, at one or more wavelengths, applied over one or more periods of time. In order to properly accomplish the photoreaction associated with the application, optical power may be delivered at or near the work piece 26 at or above one or more predetermined levels of one or a plurality of these parameters (and/or for a certain time, times or range of times).

In order to follow an intended application's parameters, the semiconductor devices 19 providing radiant output 24 may be operated in accordance with various characteristics associated with the application's parameters, e.g., temperature, spectral distribution and radiant power. At the same time, the semiconductor devices 19 may have certain operating specifications, which may be associated with the semiconductor devices' fabrication and, among other things, may be followed in order to preclude destruction and/or forestall degradation of the devices. Other components of the radiation delivery system 10 may also have associated operating specifications. These specifications may include ranges (e.g., maximum and minimum) for operating temperatures and applied electrical power, among other parameter specifications.

Accordingly, the radiation delivery system 10 may support monitoring of the application's parameters. In addition, the radiation delivery system 10 may provide for monitoring of semiconductor devices 19, including their respective characteristics and specifications. Moreover, the radiation delivery system 10 may also provide for monitoring of selected other components of the radiation delivery system 10, including its characteristics and specifications.

Providing such monitoring may enable verification of the system's proper operation so that operation of radiation delivery system 10 may be reliably evaluated. For example, radiation delivery system 10 may be operating improperly with respect to one or more of the application's parameters (e.g. temperature, spectral distribution, radiant power, and the like), any component's characteristics associated with such parameters and/or any component's respective operating specifications. The provision of monitoring may be responsive and carried out in accordance with the data received by the controller 14 from one or more of the system's components.

Monitoring may also support control of the system's operation. For example, a control strategy may be implemented via the controller 14, the controller 14 receiving and being responsive to data from one or more system components. This control strategy, as described above, may be implemented directly (e.g., by controlling a component through control signals directed to the component, based on data respecting that components operation) or indirectly (e.g., by controlling a component's operation through control signals directed to adjust operation of other components). As an example, a semiconductor device's radiant output may be adjusted indirectly through control signals directed to the power source 16 that adjust power applied to the light-emitting subsystem 12 and/or through control signals directed to the cooling subsystem 18 that adjust cooling applied to the light-emitting subsystem 12.

Control strategies may be employed to enable and/or enhance the system's proper operation and/or performance of the application. In a more specific example, control may also be employed to enable and/or enhance balance between the array's radiant output and its operating temperature, so as, e.g., to preclude heating the semiconductor devices 19 beyond their specifications while also directing sufficient radiant energy to the work piece 26, for example, to carry out a photoreaction of the application.

In some applications, high radiant power may be delivered to the work piece 26. Accordingly, the light-emitting subsystem 12 may be implemented using an array of light-emitting semiconductor devices 20. For example, the light-emitting subsystem 12 may be implemented using a high-density, light-emitting diode (LED) array. Although LED arrays may be used and are described in detail herein, it is understood that the semiconductor devices 19, and arrays 20 thereof, may be implemented using other light-emitting technologies without departing from the principles of the invention; examples of other light-emitting technologies include, without limitation, organic LEDs, laser diodes, other semiconductor lasers.

Continuing with FIG. 1, the plurality of semiconductor devices 19 may be provided in the form of arrays 20, or an array of arrays (e.g., as shown in FIG. 1). The arrays 20 may be implemented so that one or more, or most of the semiconductor devices 19 are configured to provide radiant output. At the same time, however, one or more of the array's semiconductor devices 19 may be implemented so as to provide for monitoring selected of the array's characteristics. The monitoring devices 36 may be selected from among the devices in the array and, for example, may have the same structure as the other, emitting devices. For example, the difference between emitting and monitoring may be determined by the coupling electronics 22 associated with the particular semiconductor device (e.g., in a basic form, an LED array may have monitoring LED devices where the coupling electronics provides a reverse current, and emitting LED devices where the coupling electronics provides a forward current).

Furthermore, based on coupling electronics, selected of the semiconductor devices in the array may be either/both multifunction devices and/or multimode devices, where (a) multifunction devices may be capable of detecting more than one characteristic (e.g., either radiant output, temperature, magnetic fields, vibration, pressure, acceleration, and other mechanical forces or deformations) and may be switched among these detection functions in accordance with the application parameters or other determinative factors and (b) multimode devices may be capable of emission, detection and some other mode (e.g., off) and may be switched among modes in accordance with the application parameters or other determinative factors.

As described above, radiation delivery system 10 may be configured to receive a work piece 26. As an example, work piece 26 may be a UV-curable optical fiber, ribbon, or cable. Furthermore, work piece 26 may be positioned at or near the foci of coupling optics 30 of radiation delivery system 10 respectively.

As another example, work piece 26 may include surgical instruments or target items that require sterilization and disinfection. Sterilization and disinfection may comprise killing and/or deactivating disease-causing microorganisms. In such an example, an sterilization and disinfection of the work piece may depend on illuminating the work piece surfaces with uniform UV light in three dimensions at predetermined intensity and for a predetermined time.

In a further example, radiation delivery system 10 may further include a chamber, such as a disinfection and sterilizing chamber, including one or more light guides receiving incident light from one or more UV light sources. The radiation delivery system 10 may also include a safety interlock system to activate and deactivate the light emitting-subsystem 12 when the chamber is closed and opened, respectively.

Turning now to FIG. 2, a perspective view of an example light guide 200 is shown relative to coordinate axes 290. Herein, the light guide 200 may be a part of a radiation delivery system and may transport light from the light sources to target items or work pieces positioned on a surface of the light guide. Typically, light guides are composed of optical grade materials such as acrylic resin, polycarbonate, epoxies and glass. When operated for sterilizing and disinfecting applications using UV light, the light guide 200 may be composed of material that is transparent to UV such as fused silica, fused quartz, glass compositions, polymers, and the like.

Light guide 200 may include one or more light input surfaces through which light may enter or be directed into the light guide. Herein, a first light input surface 204 may allow radiation such as UV light 210 to enter the light guide 200. Likewise, a second light input surface 206, may allow radiation such as UV light 212 to enter the light guide 200. Herein, UV light 210 and 212 may be generated by UV light sources (such as light-emitting subsystem 12 not shown in FIG. 2) capable of emitting wavelengths in the UV range (<400 nm). As an example, the UV light sources from a light-emitting subsystem 12 may emit wavelengths between 200 nm and 300 nm. The UV wavelength of the UV light sources may be selected or predetermined according to the application. As described above with respect to FIG. 1, the UV light sources may include one or more UV LEDs or arrays of UV LEDs (such as array 20 of FIG. 1). A controller, such as controller 14 of FIG. 1, may adjust the output of the UV LEDs based on the application. For example, the UV LED power may be set to a higher output level for a longer duration to sterilize the work piece.

UV light generated at the UV light sources may be coupled to the light guide 200 (not shown in FIG. 2) such that UV light may enter the light guide 200 via the one or more light input surfaces (204, and/or 206). In some examples, the UV light sources may be directly mechanically coupled to the light input surfaces of the light guide. In another example, the UV light source may be placed directly adjacent to the one or more light input surfaces of the light guide so that radiant output 24 is transmitted directly into the one or more light input surfaces. In this way, stray radiant output 24 from the UV light sources directed away from the one or more light input surfaces may be reduced. In other examples, light from a common UV light source may be partially redirected or divided using additional coupling optics (such as fibers, reflectors, and the like) to enter the light guide at each of the two opposing light input surfaces.

As shown in FIG. 2, light guide 200 may be formed from a rectangular block-like trays having a flat sheet-like aspect and including opposing pairs of parallel surfaces 204 and 206, 220 and 222, and 202 and 208. A light guide formed from a rectangular block-like trays having a flat sheet-like aspect may be advantageous as compared to other geometries at least because: the trays may provide a more stable and rigid support upon which work pieces may be placed; multiple trays may be easily stacked in a space-efficient regular manner; and recessed cutouts may be more easily formed from the flat, rectangular surfaces of the trays (e.g., the trays can be easily mounted, gripped and cut or milled into using standard tooling). The rectangular geometry of the tray may enable a decoupling of the tray from the light source, for example. The tray may be easily removed like a drawer and, when inserted into the cabinet, may be located in a position that properly aligns the input surfaces of the tray with the "fixed" LED light sources in the cabinet as shown in FIGS. 12A-B. In other examples, the light guide 200 may be formed from other geometries and may be selected based on a work piece geometry.

Light guide 200 further includes one or more cutouts 218 recessed from a surface 202 of the light guide. As shown in the example of FIG. 2, three recessed cutouts are formed from the surface of the light guide. In one example, the surface 202 may be an upper surface (in the y-direction) of the light guide and the cutout may extend along the entire width W (in the x-direction) of the light guide from front surface 220 until rear surface 222. Forming the recessed cutouts 218 in an upper surface 202 of the light guide 200 may be advantageous for stably supporting while delivering radiation to one or more work pieces therein because the work piece may more easily remain cradled in the recessed cutout. If the recessed cutouts are formed from a side surface (e.g., 220, 222) or a lower surface (208), a means for coupling or retaining the work piece to the recessed cutout such as an adhesive or mechanical coupling may be utilized.

Herein, surfaces 220 and 222 may be parallel surfaces of the light guide located opposite to one another, and may further be orthogonal to the light input surfaces 204 and 206. The surfaces 220 and 222 aid in containing the radiation within the guide until the radiation reaches a cutout (or extraction point). As will be described later with reference to FIGS. 5A and 5B, some portions of the incident light rays may have a shorter, more direct path to the recessed cutouts 218, while some portions of the light rays may have a longer, more indirect path with multiple reflections on the sidewalls before light is transmitted out of the light guide 200 at the recessed cutouts 218. The orthogonal position of the sidewalls or surfaces 220 and 222 to the light input surfaces 204 and 206 aids in retroreflecting the light rays taking the longer path back into the light guide 200 and in discouraging premature transmission of the light rays out of the light guide 200 (prior to transmission out of the light guide at the recessed cutouts 218). Further, the orthogonal position of the surfaces 220 and 222 also aids in more uniform mixing and distribution of incident light from both light input surfaces (212 and 210), for example, within the light guide 200.

The surface from which the recessed cutouts 218 are form (e.g., surface 202) may be different from the light input surfaces 204 and 206, for example. Cutout 218 may be formed on surface 202 in such a way that the surface 202 may be a discontinuous surface. For example, the surface 202 may include disjointed surface segments 202a, 202b, 202c and 202d with the one or more recessed cutouts 218 cradled between them. Herein, cutout 218 may be cradled between pairs of the disjoint surfaces (such as 202a and 202b; 202b and 202c; and 202c and 202d). The area defined by the cutout region of the light guide may represent an area where radiation may be delivered from light guide 200. For example, a work piece to be sterilized and disinfected may be positioned inside the cutout of the light guide within the curing area. The work piece may then be irradiated by UV light as described below with reference to FIGS. 5A and 5B, and FIG. 6 to sterilize and disinfect the work piece positioned inside the cutout, for example.

Thus, an example radiation delivery system may include a light guide comprising a UV transparent tray with one or more cutouts recessed from a surface of the tray, the one or more cutouts shaped to cradle one or more work pieces, and an array of light emitting elements arranged to direct radiation into a light input surface of the tray, wherein the one or more work pieces are irradiated by radiation transmitted from within the tray through recessed surfaces of the one or more cutouts. Additionally, or alternatively, each of the one or more cutouts may comprise a recessed cutout volume greater than a volume of the one or more work pieces.

Additionally, or alternatively, the one or more cutouts may be recessed from a first of two opposing parallel surfaces of the tray, the two opposing parallel surfaces being different from the light input surface.

Recessed cutouts 218 having various geometries may be formed. For example, the recessed cutouts may be formed having a partial cylindrical, partial spherical, triangular (e.g., V-grooves), rectangular, or polygonal (e.g., faceted grooves) cross section.

In the case where multiple trays or light guides are stacked on top of each other, spherical cutouts may facilitate transmission of light out both the top most and bottom most surfaces of the multiple trays or light guides as explained in detail with reference to FIG. 7. Some example geometries are shown in FIG. 10.

Figure 10A:
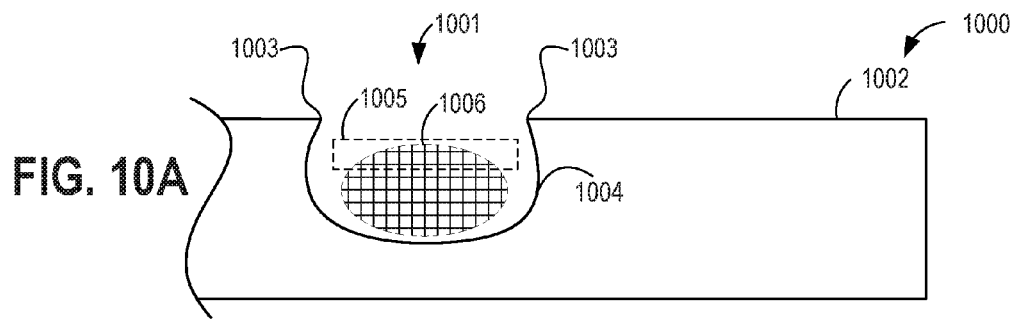
FIGS. 10A-10E illustrate partial side views of example light guides including various recessed cutouts and work pieces.
Figure 10B:
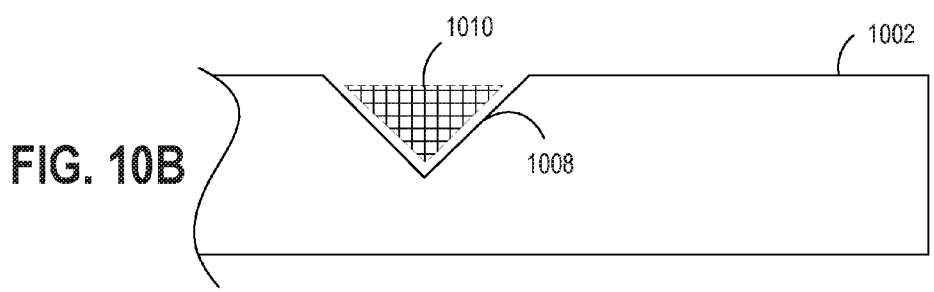
Figure 10C:
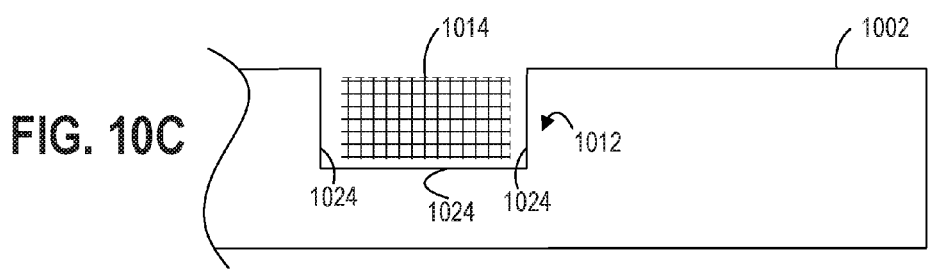
Figure 10D:
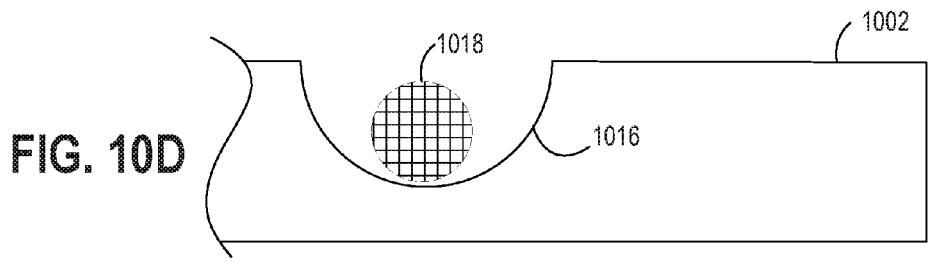
Figure 10E:
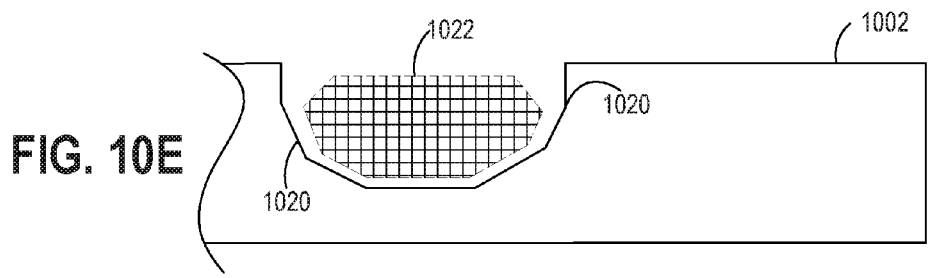

Turning now to FIGS. 10A-10E, they illustrate partial non-limiting example side views of a light guide 1002 including a recessed cutout cradling an example work piece contained therein. The particular cutout geometry may be selected according to a work piece geometry. For example, the recessed cutout may conform or partially conform to a geometry of the work piece, and a volume of the recessed cutout may be greater than a volume of the work piece. FIG. 10A shows a work piece 1006 positioned within a recessed cutout 1004 with cylindrical cross-section. Herein, the cylindrical cross-sectional geometry of the recessed cutout may cradle the work piece 1006 including a substantially cylindrical cross-section, for example. For example, a cylindrical recessed cutout may be more suitable for delivering radiation uniformly to surfaces of a cylindrical work piece such as a rod, wire, or fiber. In the example of FIG. 10A, the recessed cutout 1004 may be shaped so that recessed cutout ends 1003 may pinch in towards the work piece, which may aid in directing transmitted light through the recessed cutout to a less recessed region 1005 of the work piece 1006. In some examples, the pinching in of the recessed cutout ends 1003 may be severe enough that a recessed cutout opening 1001 may be smaller in than a cross-sectional dimension of the work piece. In this case, the work piece may be inserted and cradled by the recessed cutout by sliding the work piece longitudinally into the recessed cutout (e.g., perpendicularly into the page of FIG. 10A). Similarly, FIG. 10B shows a work piece 1010 cradled within a recessed cutout 1008 with triangular cross-section and the triangular cross-sectional geometry of the recessed cutout may cradle the work piece 1010 including substantially triangular cross-section, for example. In some examples, triangular V-grooves 1008 may aid in transmission of light incident from one side (e.g., input surface) of the light guide. FIG. 10C shows a work piece 1014 cradled within a rectangular cutout 1012. In some other examples, rectangular cutouts may be ground so that one or more of the surfaces 1024 may be ground of finished so as to function as a scattering surface to diffuse light transmitted through the recessed cutout surface from within the light guide on to the work piece. FIG. 10D shows a work piece 1018 cradled within a spherical cutout 1016. As explained earlier, spherical cutout 1016 may facilitate transmission of light out both the top most and bottom most surfaces of the multiple trays or light guides. FIG. 10E shows a work piece 1022 cradled within a faceted (polygonal) cutout 1020. Recessed cutouts 1020 comprising faceted grooves may be designed to approximate the characteristics of spherical recessed cutouts, for example.

One example recessed cutout including a cylindrical geometry (e.g., having a partial cylindrical cross section and a recessed cylindrical surface) is shown in FIG. 3. The particular cutout geometry may be selected according to a work piece geometry. As explained earlier, a cylindrical recessed cutout may be more suitable for delivering radiation uniformly to surfaces of a cylindrical work piece such as a rod, wire, or fiber. In another example, a recessed cutout having a spherical shape may be more suitable for delivering radiation uniformly to surfaces of a spherical work piece such as a bead or ball.

Turning now to FIG. 3, it illustrates a perspective view of a schematic 300 showing a method of forming cylindrical cutouts on an example light guide 302. Light guide 302 may be an example embodiment of light guide 200 of FIG. 2. Light guide 302 (hereafter also referred to as curing tray) may be composed of UV transparent material such as fused silica, fused quartz, glass materials, polymers, and the like. Curing tray 302 may include a surface 306 on which cutouts 316 (three non-limiting examples of cutouts is shown in FIG. 3) may be generated. Cutouts 316 may be created by chemically or mechanically etching grooves on the surface of the curing tray 302. For example, the curing tray may be machined using lasers to generate grooves of cylindrical patterns. Furthermore, cylindrical cutouts 316 may be formed by drilling or milling into surface 306 with cylindrical tooling as schematically represented by cylinders 304. Specific tray cutout geometries may be manufactured in a number of ways such as laser etching, scribing and the like. The optical surfaces may be machined; (such as, CNC milling), depending on the depth and required tolerances of the recessed surfaces or the faces of the recessed cutouts 218. The cutout may then be polished (fire polished or other polishing methods) to produce an optically smooth surface, or further ground to produce a scattering surface. Chemical etching may also be done depending on the type of material. The tray may be molded out of material transparent to the irradiating wavelength such as some glasses or polymers, for example. One non-limiting example of such a polymer is TOPAS® 8007 manufactured by TOPAS Advanced Polymers.

In schematic 300, the cutout 316 may span the entire width W of the curing tray 302. In other examples the cutout may span a partial width less than width W. The shape or profile of the recessed surface of the cutout 316 may depend on an outward curvature of the cylinder 304 used to form the cutout, for example. Herein, the spacing between the cutouts, the number of cutouts, and the depth to which the cutouts are generated on the surface of the curing tray may be adjusted based on a size of the work piece that is to be irradiated. Furthermore, the spacing, the depth and the number of cutouts may further be adjusted to generate uniform illumination of the work piece positioned inside the cutout as described later with reference to FIG. 5.

The size and dimensions of the recessed cutouts 316 may be selected according to the size and dimensions of the one or more work pieces to be irradiated. In order to irradiate larger work pieces, the cutout 316 may be formed more deeply into the curing tray 302, while shallower cutouts may be formed for smaller work pieces, for example. In other examples, the volume and dimensions of the one or more recessed cutouts may be selected to be greater than the volume and dimensions of the one or more work pieces so that the one or more work pieces may be contained within the one or more recessed cutouts while delivering radiation thereto. For example, width W, depth D, and cross-sectional areas of the recessed cutout 316 may be greater than a width, depth, and cross-sectional area of the work piece. UV light may enter the curing tray 302 via opposing light input surfaces 312 and 314. Herein, the surface 306 including the recessed cutouts may be different from the one or more light input surfaces 312 and 314. Thus, a work piece may be placed within the cutouts 316 formed by the cylinders 304, and further irradiated with UV light entering the light guide 302 via light input surfaces and guided to the work piece through surfaces of the recessed cutouts 316.

Tuning now to FIG. 4, it illustrates a perspective view of a schematic view 400 showing a method of forming spherical cutouts on an example light guide 402. Light guide 402 may be an example embodiment of light guide 200 of FIG. 2. Similar to light guide 302 of FIG. 3, light guide 402 (also referred to as curing tray) may be composed of UV transparent material such as fused silica, fused quartz, glass materials, polymers, and the like. Curing tray 402 may include a surface 408 on which cutouts 416 (nine non-limiting examples of cutouts is shown in FIG. 3) may be generated. Cutouts 416 (herein also referred to as recessed cutouts) may be created by chemically or mechanically etching spherical wells on the surface of the curing tray 402. For example, the curing tray may be machined using lasers to generate a single or multiple spherical wells. Furthermore, spherical recessed cutouts 416 may be formed by drilling or milling into surface 408 with spherical tooling as schematically represented by spheres 414. In the example of FIG. 4, the spherical cutouts are generated in a two-dimensional array pattern. The spherical cutouts may be manufactured by molding glass or polymer materials that have a high transmission at the irradiating wavelength. The cutouts may be spherical, polygons, or faceted deviations of those shapes, and the like.

In schematic 400, the recessed cutouts 416 may be positioned on discrete locations along surface 408 of the curing tray 402. The recessed cutouts 416 may not continuously span the entire width of the curing tray, but may form discrete locations on the surface of the curing tray where one or more work pieces may be positioned for subsequent irradiation, for example, for sterilization and disinfection via UV irradiation. The shape and the profile of the recessed surface of the cutout 416 may depend on an outward curvature of the spheres 414 used to form the cutout, for example. Herein, the spacing between the cutouts, the number of cutouts, and the depth to which the cutouts are generated on the surface of the curing tray may be adjusted based on a size of the work piece that is to be irradiated. Furthermore, the spacing, the depth and the number of cutouts may further be adjusted to generate uniform illumination of the work piece positioned inside the cutout as described later with reference to FIG. 5.

In order to irradiate larger work pieces, the recessed cutout 416 may be formed more deeply into the curing tray 402, while shallower cutouts may be formed for smaller work pieces, for example. In other examples, the volume and dimensions of the one or more recessed cutouts may be selected to be greater than the volume and dimensions of the one or more work pieces so that the one or more work pieces may be contained within the one or more recessed cutouts while delivering radiation thereto. For example, width W, depth D, and cross-sectional areas of the recessed cutout 416 may be greater than a width, depth, and cross-sectional area of the work piece. UV light may enter the curing tray 402 via opposing light input surfaces 412 and 410. Herein, the surface 408 including the recessed cutouts may be different from the one or more light input surfaces 412 and 410. Thus, a work piece may be placed within the recessed cutouts 416 formed by the spheres 414, and further irradiated with radiation, for example with UV light, entering the light guide 402 via light input surfaces and guided to the work piece through surfaces of the recessed cutouts 416.

Turning now to FIG. 5A, it illustrates a partial cross-sectional view of a light guide 500 including a light input surface 502, and a recessed cutout 530 cradling an example work piece 580 contained therein. Work piece 580 is shown positioned in a middle portion of recessed cutout 530. Centering work piece 580 within recessed cutout 530 may aid in increasing an amount of radiation directed on to the work piece 580 from light guide 500. Work piece 580 may be cradled and may rest within recessed cutout 530 such that work piece 580 contacts recessed surface 532. Recessed cutout 530 is formed from a first surface 504 of a pair of opposing parallel surfaces of the light guide. In one example, the first surface 504 may include an upper surface (positioned at a larger y-coordinate of coordinate axes 590) of the light guide and a second surface 506 of the pair of opposing parallel surfaces may include a lower surface (positioned at a smaller y-coordinate). As described above with reference to FIGS. 2-4, recessed cutout 530 may fully or partially span a width dimension of light guide 500 in the x-direction. Furthermore, the dimensions of recessed cutout 530 may be selected such that a work piece 580 to be irradiated may be placed inside the recessed cutout 530 such that a volume of the recessed cutout 530 is greater than a volume of the work piece 580. In addition, a width and depth of the recessed cutout 530 may be greater than a width and depth of the work piece 580. Furthermore, light guide 500 may comprise a linear or two-dimensional array of recessed cutouts from one of its surfaces (e.g., first surface 504).

FIG. 5A further shows radiation, such as radiant output from a light source (e.g., UV light rays), entering light guide 500 at a light input surface 502 and being guided within the light guide 500 through recessed surface 532. Radiation such as UV light may be guided through the light guide 500 via total internal reflection, the radiation undergoing multiple total internal reflections at first and second surfaces (504, 506) of the light guide 500. In addition, the radiation guided through light guide 500 may undergo multiple total internal reflections at other surfaces of the light guide 500. For example, with reference to FIG. 2, radiation may be guided within light guide 200 via total internal reflection at surfaces 220, 222, 208, and 202. In particular, the incident radiation (e.g., UV light) at surfaces 504 and 506 of light guide 500 may obey total internal reflection (TIR) and may thereby be contained within the light guide; however incident radiation (e.g., UV light) at the recessed surface 532 may violate TIR and thereby be transmitted through recessed surface 532 thereby exiting the light guide 500 and irradiating a work piece 580 positioned within the recessed cutout 530. Radiation obeying TIR at a particular surface (e.g., light guide to air interface) may include radiation incident at an incident angle less than the critical angle for TIR, whereas radiation violating TIR at a particular surface may include radiation incident at an incident angle greater than the critical angle for TIR. Radiation entering light guide 500 at light input surface 502 does not undergo TIR because the radiation is moving from a medium (e.g., air) of lower refractive index to a medium of higher refractive index.

Light guide 500 includes a light input surface 502 at which UV light may enter the light guide. In FIG. 5A, only one of the light input surfaces is shown. However, additional light input surface (parallel and opposite to light input surface 502) may exist in the light guide as explained earlier with reference to FIG. 2. Light guide 500 may include one or a plurality of cutouts formed on a first surface 504 of the light guide. One cutout 514 is shown as a non-limiting example. The cutout 514 may form a recessed volume within the cutout such that the recessed volume of the cutout may be larger than a volume of one or more work pieces 580 placed within the cutout. Thus, a work piece 580 cradled within the cutout may be positioned fully inside a volume the cutout.

A few example light rays are shown in FIG. 5A. Radiant output (e.g., UV radiation) from one or more light sources may be directed into light guide 500 through light input surface 502. UV light ray 514 (hereafter referred to as ray 514) from the one or more light sources may thus originate at light input surface 502 of the light guide. Ray 514 may travel from the light input surface 502 and may be incident at first surface 504 at angle cu, as shown. Because angle cu may be greater than a critical angle for TIR, ray 514 may undergo total internal reflection at first surface 504 and may be reflected (as ray 516) back in to the light guide 500.

Thus, ray 514 may be totally internally reflected at first surface 504, generating ray 516. Similarly, ray 516 may be totally internally reflected at a second surface 506, the second surface 506 positioned parallel and opposite to first surface 504, for example, thereby generating another reflected ray 518. However, ray 518 may be incident at the recessed surface 532 at an angle $\alpha_2$ lower than the critical angle, thereby violating the criteria for total internal reflection, as explained above. As a result, ray 518 may not be reflected back in the light guide 500, and may instead be transmitted into the volume of the recessed cutout 530 on to work piece 580, for example. In this way, one or more work pieces 580 positioned within the recessed cutout 530 may be irradiated by radiation escaping from the light guide 500 through the recessed surface 532.

Similar to ray 514, ray 508 originating at light input surface 502 may undergo total internal reflection when incident at second surface 506 thereby generating reflected ray 510 which stays within the light guide 500. However, ray 510 may be incident at the recessed surface 530 at an angle lower than the critical angle, for example, thereby violating the criteria for total internal reflection. As a result, ray 510 may not be reflected back inside the light guide 500, and may be transmitted into the volume of the recessed cutout 530 and on to work piece 580, for example. A portion of the radiation within the light guide 500, including ray 522, that is incident at recessed surface 532 at an angle greater than the critical angle for TIR, may undergo TIR at recessed surface 532. After undergoing TIR, the radiation (e.g., ray 524) may be guided via additional TIR back to the recessed surface 532 where it may be transmitted through recessed surface 532 to the work piece 580. In another example, as shown in FIG. 5A, ray 524 may be incident at another external surface of light guide 500, such as second surface 506, at an angle less than the critical angle. Consequently, ray 524 may be transmitted out of the light guide 500. In this manner a portion of the radiation input at light input surface 502 may be lost without being directed to work piece 580. Another portion of the radiation within the light guide 500, including ray 526, that is incident at recessed surface 532 at an angle less than the critical angle for TIR, may be transmitted through recessed surface 532, but may not be incident at a work piece 580 contained within the recessed cutout 530, as shown.

Turning now to FIG. 5B, it illustrates another embodiment of light guide 500 including a pair of reflective surfaces 570 and 572. Reflective surface 570 may be positioned to be directly adjacent to and facing first surface 504 and reflective surface 572 may be positioned to be directly adjacent to and facing second surface 506. Reflective surfaces 570 and 572 may aid in reducing radiation losses due to transmission of radiation originating within the light guide 500 out from first surface 504 and second surface 506. For example, as shown in FIG. 5A, a portion of the radiation inside light guide 500, including ray 524, may be lost due to transmission out of second surface 506. As shown in FIG. 5B, by positioning reflective surface 572 directly adjacent to and facing second surface 506, ray 524 may instead be retroreflected back inside light guide 500 through recessed surface 532 and on to work piece 580.

Furthermore, by positioning reflective surface 570 directly adjacent to and facing first surface 504, including facing above recessed cutout 530 (where first surface 504 is discontiguous), radiation losses from light guide 500 due to transmission of radiation out from recessed surface 532 that is not incident at a surface of the work piece 580 may be reduced. For example, as shown in FIG. 5A, a portion of the radiation inside light guide 500, including ray 526, may be transmitted through recessed surface 532, but may not be incident at work piece 580 and may be lost. As shown in FIG. 5B, by positioning reflective surface 570 directly adjacent to and facing first surface 504, ray 526 may instead be retroreflected back on to work piece 580 or back into light guide 500.

Because work piece 580 may be positioned inside a recessed cutout 530, the work piece 580 may not impinge on the reflective surface 570, thereby allowing the reflective surface 570 to be positioned directly adjacent to first surface 504. Positioning reflective surface 570 directly adjacent to first surface 504 further reduces radiation losses from light guide 500 by mitigating radiation transmission from the light guide 500 to any space between first surface 504 and reflective surface 570.

Thus, an example UV light guide for irradiating one or more work pieces may include one or more cutouts recessed from a surface of the UV light guide, the one or more cutouts shaped to cradle the one or more work pieces, wherein recessed surfaces of the one or more cutouts comprise UV transmissive surfaces for transmitting UV light from within the UV light guide on to the one or more work pieces. Additionally, or alternatively, the one or more cutouts may comprise a recessed cutout volume greater than a volume of the one or more work pieces.

Additionally, or alternatively, the example UV light guide may further include a light input surface for directing UV light into the UV light guide, and two opposing parallel surfaces different from the light input surface, wherein the one or more cutouts are recessed from a first of the two opposing parallel surfaces. Additionally, or alternatively, the example UV light guide may include a first UV reflective surface facing the first of the two opposing parallel surfaces and additionally, or alternatively, further include a second UV reflective surface facing a second of the two opposing parallel surfaces as explained below. Additionally, or alternatively, one or more a width, a depth, and cross-sectional areas of the recessed surfaces may be greater than one or more of width, depth, and cross-sectional areas of the work pieces.

By additionally including multiple UV reflective surfaces and positioning them above and below the work piece as shown in FIG. 6, UV light may be recycled back onto the work piece. In this way, the power of UV light incident on the work piece may be increased. In addition, the entire surface area of the work piece may be exposed to UV light, thereby sterilizing and disinfecting the entire work piece surface area.

Turning now to FIG. 6, it illustrates a partially exploded view 600 including a single light guide 602 sandwiched between two reflective surfaces relative to coordinate axes 625. Light guide 602 may be an example embodiment of light guide 200 shown in FIG. 2. Light guide 602 may also be example embodiments of curing tray 302 shown in FIG. 3, and curing tray 402 shown in FIG. 4.

Specifically, a first reflective surface 604 may be positioned facing first surface 616, which may be a first of two opposing parallel surfaces from which the recessed cutouts 608 are formed, for example. In addition, a second reflective surface 606 may be positioned facing a second surface 614, which may be a second of the two opposing parallel surfaces. The reflective surfaces 604 and 606 may reflect incident radiation (e.g., UV light), and herein also be referred to as reflective surfaces. In the partially exploded view 600, the first and the second reflective surfaces are shown as being peeled back from the first surface 616 of the light guide for illustrative purposes. The first reflective surface 604 may be positioned to be directly adjacent to and facing first surface 616 of the light guide 602. As shown in FIG. 6, one or more recessed cutouts 608 are formed from first surface 616. First surface 616 may thus be a discontiguous surface. Similarly, the second reflective surface 606 may be positioned to be directly adjacent to and facing second surface 614 of the light guide 602. Herein, the second surface 614 may be positioned opposite to first surface 616 from which the one or more recessed cutouts 608 are formed.

First and second reflective surfaces 604 and 606 may aid in reducing radiation losses due to transmission of radiation originating within the light guide 602 out from first reflective surface 604 and second reflective surface 606. As explained earlier with reference to FIGS. 5A and 5B, a portion of the radiation inside light guide 602, may be lost due to transmission out of second reflective surface 606. By positioning second reflective surface 606 directly adjacent to and facing second surface 614, radiation may instead be retroreflected back inside light guide 602 through recessed cutouts 608 and on to work piece (not shown in FIG. 6).

Furthermore, by positioning first reflective surface 604 directly adjacent to and facing first surface 616, including facing above recessed cutouts 608, radiation losses from light guide 602 due to transmission of radiation out from recessed surfaces of the recessed cutouts 608 (along Y-axis) that is not incident at a surface of the work piece may be reduced.

Because one or more work pieces may be positioned inside the one or more recessed cutouts 608, the work piece may not impinge on the first reflective surface 604, thereby allowing the first reflective surface 604 to be positioned directly adjacent to first surface 616. Positioning first reflective surface 604 directly adjacent to first surface 616 further reduces radiation losses from light guide 602 by mitigating radiation transmission from the light guide 602 to any space between first surface 616 and first reflective surface 604.

In some examples, the first and the second reflective surfaces 604 and 606 may be composed of the same reflective material such as polished aluminum. In some more examples, the reflective surfaces may be coated with a paint that is highly reflective to radiation such as UV light. In certain embodiments, the first reflective surface 604 may be of a different composition than the second reflective surface 606. In one example, the bottom reflective surface may be specular reflecting, thereby non-diffusely reflecting light back into the light guide, and the top reflective surface may be diffuse reflecting, thereby diffusing and spreading the light around the target work piece positioned in the cutout.

Thus, by positioning reflecting surfaces on either side of the light guide, the one or more work pieces cradled within the recessed surfaces of the light guide 602 may be illuminated with more uniform radiation (612) on external surfaces of the work piece, thereby increasing the irradiated surface area of the work piece.

FIG. 7 illustrates an example light guide comprising a plurality of trays and reflective surfaces 726, 728 facing opposing parallel surfaces of the light guide 700 relative to coordinate axes 725. Herein, a partially exploded view of light guide 700, illustrates two trays positioned one on top of the other with reflective surfaces 726, 728 positioned on both ends of the stack. In other examples more than two trays may be stacked, having the reflective surfaces 726 and 728 positioned on either end of the stack. As shown in FIG. 7, the reflective surfaces are shown as being peeled back from the light guide for illustrative purposes only; the reflective surfaces 728 and 726 may be positioned directly adjacent to a first surface 712 of the second tray 704 and a bottom surface 706 of the first tray 702, respectively The light guide 700 includes a first tray 702, stacked with on a second tray 704. Each of the first tray 702 and second tray 704 may be example embodiments of light guide 602 shown in FIG. 6. As described above, in other examples, more than two trays may be stacked (along Y-direction, for example).

The first tray 702 may include a first surface 708. One or more recessed cutouts 724 may be formed from the first surface 708. The one or more recessed cutouts 724 may span the entire width of the first tray 702 along X-axis, as shown in FIG. 7. In other examples, the recessed cutouts may span a partial width of the first tray 702 along the X-axis. Various geometries of the recessed cutouts may be possible, as explained earlier with reference to FIGS. 2-4 and 10. The first tray 702 may include light input surfaces 714 and 720 positioned at opposite ends of the tray.

The second tray 704 may include a first surface 712. One or more recessed cutouts 722 may be formed from the first surface 712. Similar to recessed cutouts 724 of the first tray 702, the one or more recessed cutouts 722 of the second tray 704 may span the entire width of the second tray 704 along the X-axis, as shown in FIG. 7. In other examples, the recessed cutouts may span a partial width of the second tray 704 along the X-axis. Various geometries of the recessed cutouts may also be possible (as shown in FIG. 10A-E). The second tray 704 may include light input surfaces 716 and 718 positioned at opposite ends of the tray.

The second tray 704 may be positioned or stacked on the first tray 702 such that surface 710 of the second tray 704 may be flush with the first surface 708 of the first tray 702. Further, the light input surfaces of each of the trays may also be flushly aligned. Herein, the light input surfaces 714 and 720 of the first tray 702 may also be flushly aligned with the light input surfaces 716 and 718 of the second tray 704, respectively. Furthermore, an array of light emitting elements (not shown in FIG. 7) may be arranged to direct radiation into one or more of the light input surfaces of each of the first tray 702 and the second tray 704.

As such, the trays of the stack may include a bottom tray and a top tray and may further include plurality of trays positioned between the bottom tray and the top tray. The trays positioned between the top and the bottom tray may not include reflective surfaces. However the top tray may include a reflective surface positioned on the upper surface of the top tray and the bottom tray may include a reflective surface at the lower surface of the bottom tray. As such, the trays may be aligned such that light emitted from the bottom of each tray of the stack (except the bottom most tray of the stack) may illuminate the recessed cutouts and the work pieces positioned therein of the tray directly below. Furthermore, the trays may be aligned such that light emitted from the top of each tray of the stack (except the top most tray of the stack) may be transmitted into the trays positioned directly above.

However, for the trays that are at the ends of the stack, namely the bottom end and the top end of the stack, a reflective surface may be included on one of the surfaces of the tray. For example, a reflective surface 726 may be positioned adjacent to and facing bottom surface 706 of the first tray 702. Similarly a reflective surface 728 may be positioned adjacent to and facing first surface 712 of the second tray 704. Thus, incident radiation transmitted through a bottom surface 706 of the first tray 702 may be incident on the first reflective surface 726 and may be retroreflected back towards the work piece located inside the recessed cutouts 724 of the first tray 702 (which is shown as the bottom tray of the stack), for example. Similarly, light transmitted from the first surface 712 of the second tray 704 (which is shown as the top tray of the stack) may be reflected by the UV reflective surface 728 back onto the work piece located within the recessed cutouts 722 of the second tray 704, for example.

In this manner, the radiation delivery system may include a plurality of the trays arranged in a stack, wherein the first of the two opposing parallel surfaces of each of the trays is positioned flush with the second of the two opposing parallel surfaces of an adjacent tray in the stack, the light input surfaces of each of the trays are flushly aligned, and the array of light emitting elements is arranged to direct radiation into the light input surfaces of each of the UV transparent trays. Additionally, or alternatively, the radiation delivery system may further include a first reflective surface positioned adjacent to and facing the first of the two opposing parallel surfaces of a tray at an end of the stack, wherein incident UV light at the first reflective surface is reflected back to the first of the two opposing parallel surfaces of the tray at the end of the stack. Additionally, or alternatively, the radiation delivery system may include a second reflective surface positioned adjacent to and facing the second of the two opposing parallel surfaces of a tray at another end of the stack, wherein incident UV light at the second reflective surface is reflected back to the second of the two opposing parallel surfaces of the tray at the other end of the stack.

Figure 8:
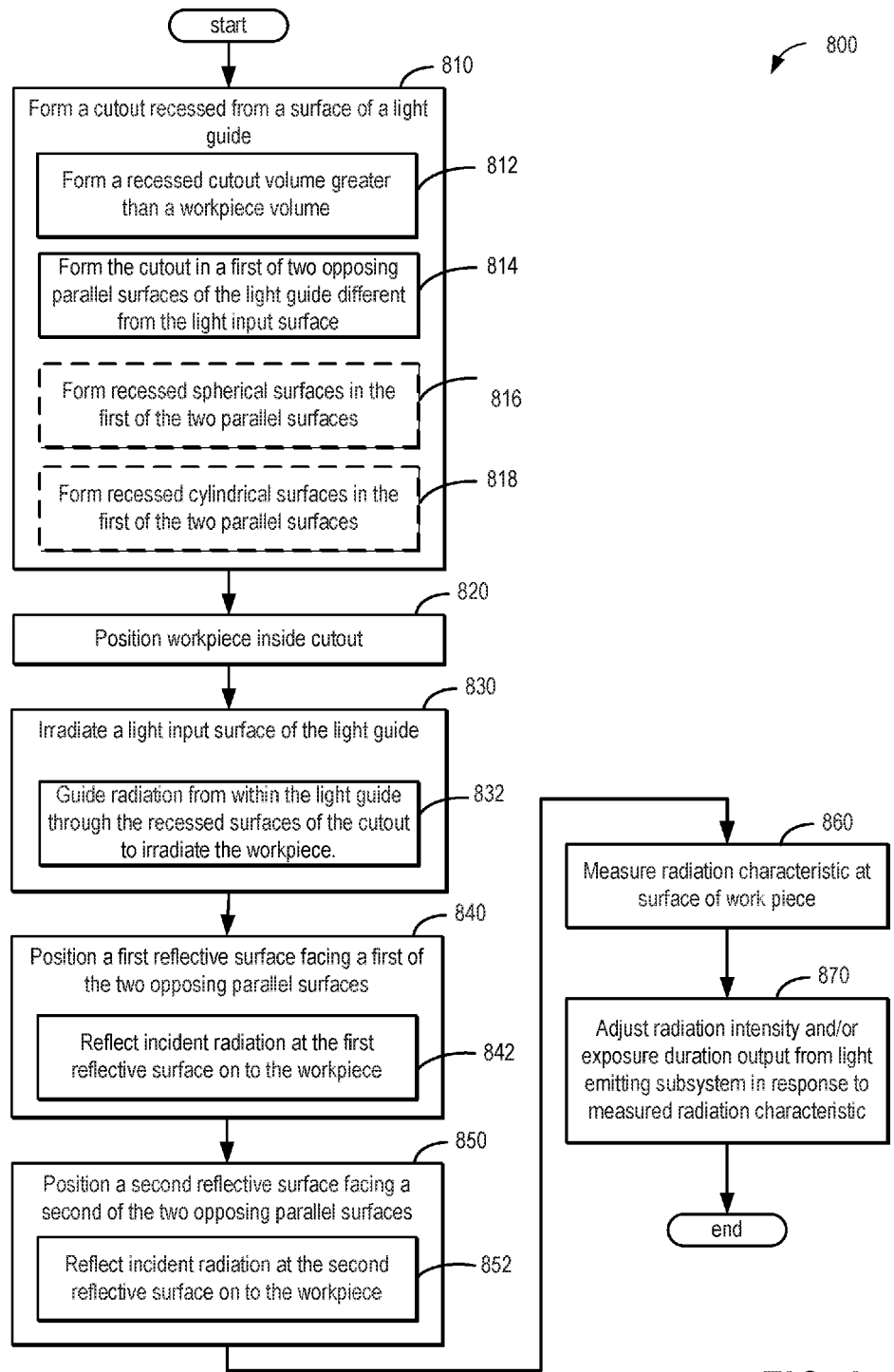
FIG. 8 illustrates a flowchart of an example method of irradiating work pieces with a radiation delivery system including a light guide.

Turning now to FIG. 8, an example method 800 of irradiating work pieces, positioned inside cutouts recessed on the surface of the light guide, is shown. Method 800 begins at 810, where a cutout recessed from a surface of a light guide may be formed. Forming the cutout at 810 may further include forming a recessed cutout volume greater than a work piece volume at 812. Further, the cutout may be formed in a first of two opposing parallel surfaces of the light guide at 814. As such, the cutout may be formed on a surface that is different from the light input surface of the light guide, for example. Method 810 may include forming recessed spherical surfaces in the first of the two parallel surfaces at 816. Method 810 may also include forming recessed cylindrical surfaces on the first of the two parallel surfaces of the light guide at 818. Various other geometries of the cutouts may also be formed on the light guide, including but not limited to cylindrical geometries, spherical geometries V-shaped geometries, faceted groove geometries, and the like as shown in FIGS. 10A-E. In some examples, the cutout may span the width of the light guide or may be formed as arrays of isolated structures recessed into the first surface of the light guide.

Method 800 then proceeds to 820 where a work piece may be positioned inside the cutout. As described above, a volume of the work piece may be less than a volume of the cutout and a width and depth of the work piece may be less than a width and depth of the cutout, respectively. As such, the work piece may be positioned inside the cutouts. Positioning the work piece inside the cutout may include approximately centering the work piece within the cutout to increase an amount and uniformity of radiation incident on the work piece surfaces. As described above, one or more cutouts may be formed in the light guide to accommodate one or more work pieces. Each of the one or more cutouts may accommodate one or more work pieces.

Method 800 then proceeds to 830 where the light input surface of the light guide may be irradiated with radiation. In one example, the radiation may comprise UV light for curing, sterilizing, and/or disinfecting the work piece. For example, irradiating the light input surface of the light guide may include supplying power to one or more radiation sources, and positioning the light sources directly adjacent to the light input surfaces of the light guide. Positioning the light sources directly adjacent to the light input surfaces may reduce radiation lost as stray light from the light sources that is not directed into the light input surfaces. Irradiating the light input surface of the light guide may further include guiding the radiation from within the light guide through recessed surfaces of the cutout to irradiate the work piece at 832. Radiation may be guided within the light guide via total internal reflection (TIR) at the external surfaces of the light guide. Furthermore, radiation incident at recessed surfaces of the recessed cutout may violate TIR and may exit the light guide and irradiate the work piece positioned within the recessed cutout.

Method 800 then proceeds to 840 where a first reflective surface may be positioned facing the first of the two opposing parallel surfaces. Next at 842, incident radiation may be reflected at the first reflective surface on to the work piece. Then, method 800 proceeds to 850 where a second reflective surface may be positioned facing a second of the two opposing parallel surfaces. Next at 852 incident radiation may be reflected at the second reflective surface on to the work piece.

Method 800 continues at 860 where it may measure a radiation characteristic at the surface of one or more work pieces. The radiation characteristic may include a characteristic of the emitted radiation such as radiation intensity or irradiance. In other examples the radiation characteristic may include a characteristic of the irradiated work piece such as temperature, extent of cure, composition, and the like. At 870, method 800 adjusts the radiation output from the light emitting subsystem in response to the measured radiation characteristic. As an example, the radiation output intensity and/or exposure duration of one or more light sources may be altered. After 870, method 800 ends.

Thus, an example method of irradiating a work piece may include forming a cutout recessed from a surface of a light guide, positioning the work piece inside the cutout, irradiating a light input surface of the light guide with UV light, and guiding the UV light from within the light guide through recessed surfaces of the cutout to irradiate the work piece. Additionally, or alternatively, forming the cutout may include forming a recessed cutout volume greater than a work piece volume. Additionally, or alternatively, forming the cutout may include forming the cutout in a first of two opposing parallel surfaces of the light guide, the two opposing parallel surfaces being different from the light input surface. Additionally, or alternatively, the method may include positioning a first reflective surface facing the first of the two opposing parallel surfaces and reflecting incident UV light at the first UV reflective surface on to the work piece. Additionally, or alternatively, the method may include positioning a second reflective surface facing a second of the two opposing parallel surfaces and reflecting incident UV light at the second UV reflective surface on to the work piece. Additionally, or alternatively, forming the cutout may include forming recessed spherical surfaces in the first of the two opposing parallel surfaces. Additionally, or alternatively, forming the cutout may include forming recessed cylindrical surfaces in the first of the two opposing parallel surfaces. Additionally, or alternatively, the method may include forming a plurality of cutouts in the first of the two opposing parallel surfaces.

UV radiation may undergo multiple total internal reflection as explained earlier, and the UV radiation may be trapped within the light guide. As such, TIR may be violated only at the surface of the embedded cutouts. At such locations, the radiation may exit the light guide and irradiate the work piece positioned within the embedded cutout.

Figure 11A:
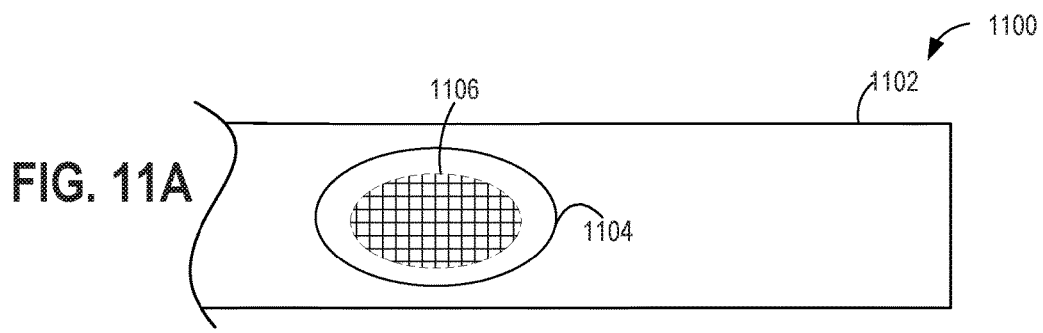
FIGS. 11A-11E illustrate partial side views of example light guides including various embedded cutouts and work pieces.
Figure 11B:
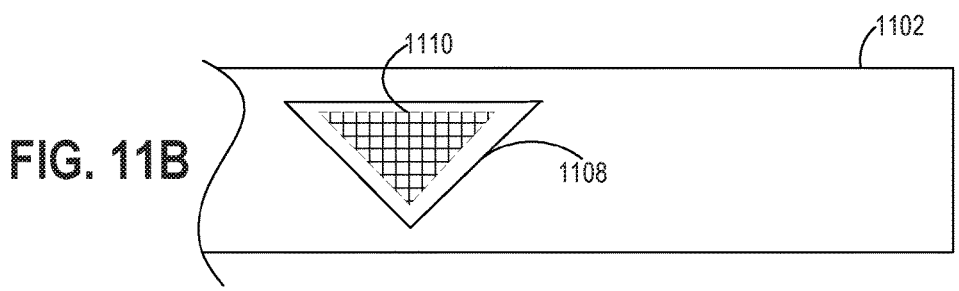
Figure 11C:
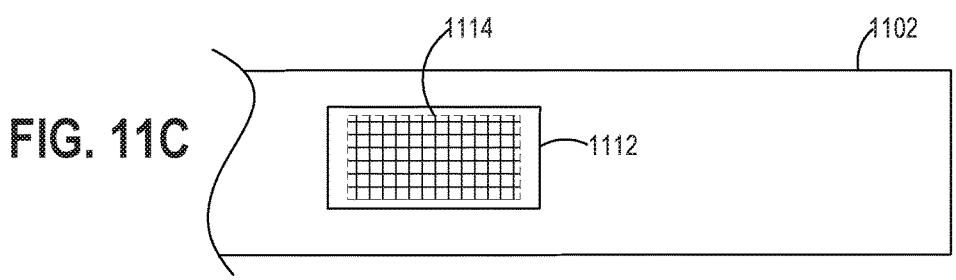
Figure 11D:
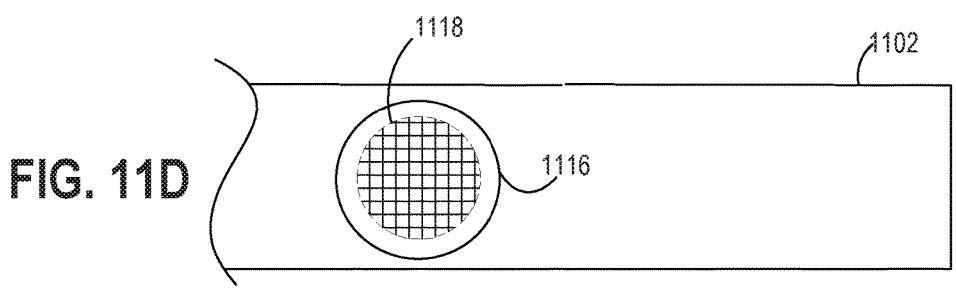
Figure 11E:
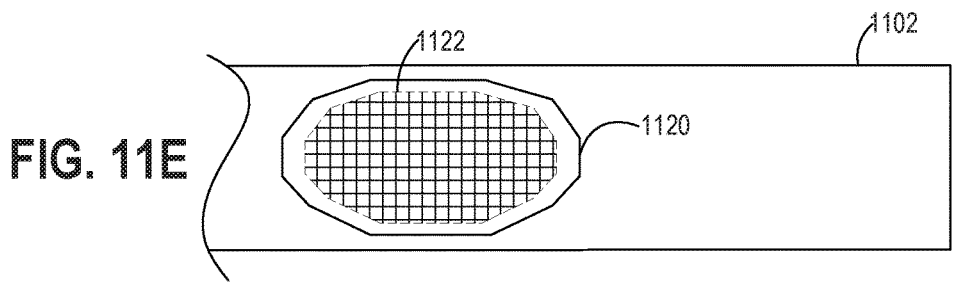
Figure 12A:
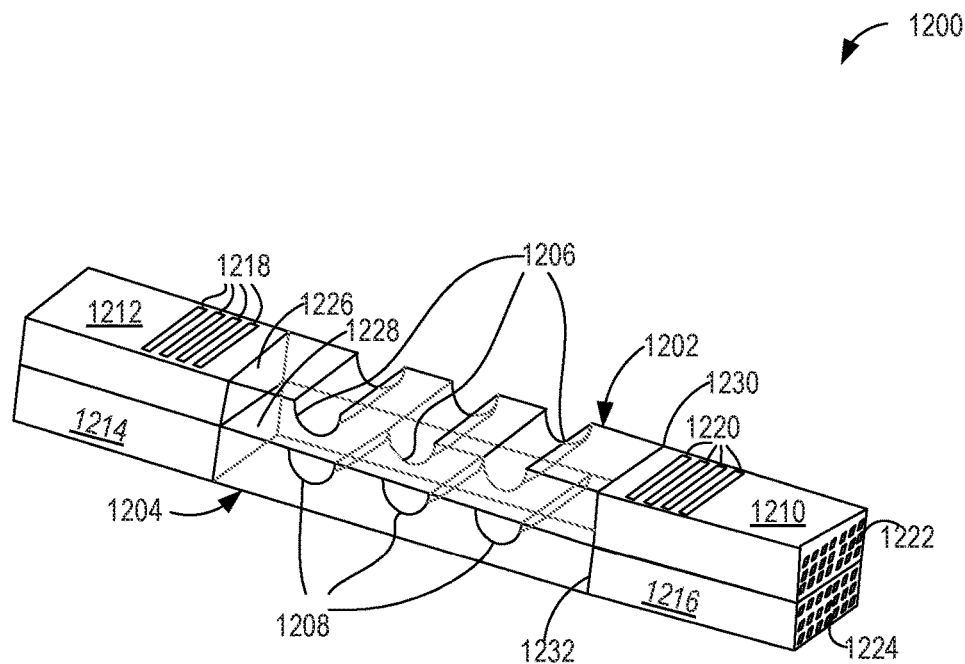
FIGS. 12A-B illustrate perspective views of an example cabinet including the multiple trays and multiple cutouts, and radiation delivery systems positioned to direct radiation into the light guides.
Figure 12B:
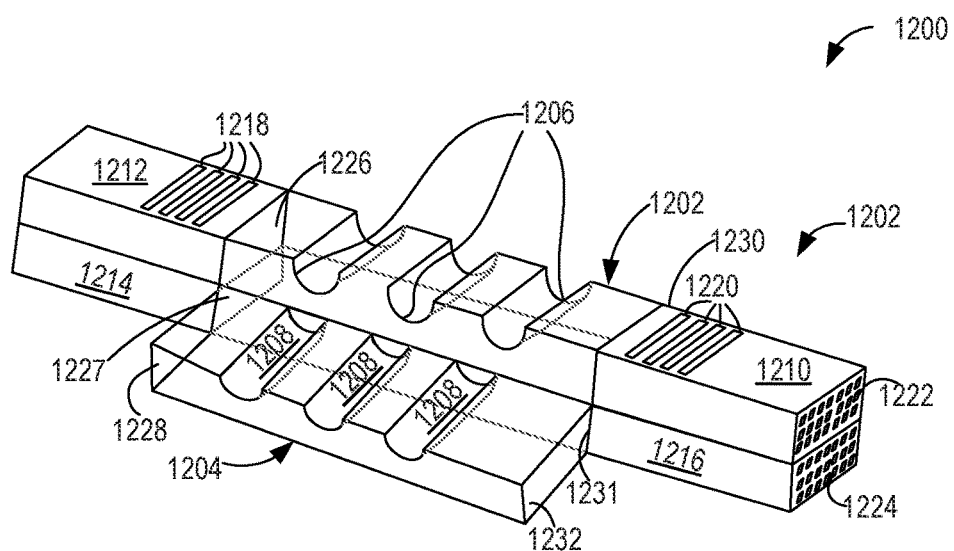

Some example geometries of embedded cutouts are shown in FIGS. 11A-11E. Turning now to FIGS. 11A-11E, they illustrate partial side views of example light guides 1102 including an embedded cutout cradling an example work piece contained therein. The particular cutout geometry may be selected according to a work piece geometry. For example, the embedded cutout may conform or partially conform to a geometry of the work piece, and a volume of the embedded cutout may be greater than a volume of the work piece. FIG. 11A shows a work piece 1106 positioned within an embedded cutout 1104 with cylindrical cross-section. Herein, the cylindrical cross-sectional geometry of the embedded cutout may engulf the work piece 1106, for example. For example, a cylindrical embedded cutout may be more suitable for delivering radiation uniformly to surfaces of a cylindrical work piece such as a rod, wire, or fiber. In this case, the work piece may be inserted and engulfed by the embedded cutout by sliding the work piece longitudinally into the embedded cutout (e.g., the longitudinal axis of the embedded cutout may be perpendicular into the page of FIG. 11A). Similarly, FIGS. 11B-11E show examples of work pieces 1110, 1114, 1118, and 1122 cradled within respective embedded cutouts 1108, 1112, 1116, and 1120 having a triangular, rectangular, circular, and faceted polygonal cross-section, respectively. The cross-sectional geometry of the embedded cutouts 1104, 1108, 1112, 1116, and 11120 may engulf or cover the respective work pieces 1106, 1110, 1114, 1118, and 1122. In some examples, the embedded cutouts may extend along the full width of the light guide. As such, a work piece may be enclosed by the light guide at external surfaces of the work piece except at end surfaces where the work piece is exposed to the widthwise openings of the embedded cutout in the light guide. In other examples, the embedded cutouts may extend only to a certain distance along the width of the light guide. As such, a work piece may be enclosed by the light guide at external surfaces of the work piece except an end surface where the work piece is exposed to the mouth of the embedded cutout. FIG. 11E shows a work piece 1122 embedded within a faceted (polygonal) cutout 1120. Embedded cutouts 1120 comprising faceted grooves may be designed to approximate the characteristics of spherical recessed cutouts, for example.

Turning now to FIGS. 12A-B, they illustrate perspective views of an example cabinet 1200 comprising one or more radiation delivery systems and multiple light guides (herein also referred to as trays) with cutouts. As shown the cutouts comprise one or more recessed cutouts, however in other examples, the cutouts may comprise one or more embedded cutouts. For illustrative purposes, the cabinet 1200 comprises two light guides each including three recessed cutouts. However, as explained earlier, any number of light guides with multiple types of recessed and/or embedded cutouts may be stacked in the cabinet.

The cabinet 1200 may include one or more radiation delivery systems 1210, 1212, 1214, and 1216 (such as radiation delivery system 10 of FIG. 1), whose position in the cabinet 1200 may be fixed. Herein, the radiation delivery systems 1212 and 1214 may be stacked on top of one another while radiation delivery systems 1210 and 1216 may be stacked on top of one another, on an opposite side of the light guides (e.g., trays 1202 and 1204) to the radiation delivery systems 1212 and 1214, respectively. In addition, the radiation delivery systems 1210 and 1212 may be positioned such that radiation exiting the radiation delivery systems may be directed into light input surfaces 1230 and 1226 at opposite sides of the tray 1202. Similarly, radiation delivery systems 1214 and 1216 may be positioned such that radiation exiting the radiation delivery systems may be directed into light input surfaces 1228 and 1232. Radiation may exit the radiation delivery system 1210 along light input surface 1230 (hidden in this perspective view), and radiation may exit radiation delivery system 1216 along light input surface 1232 (also hidden in this perspective view). Likewise, radiation may exit radiation delivery system 1212 along light input surface 1226, and radiation may exit radiation delivery system 1214 along light input surface 1228. Herein, light input surfaces 1230 and 1232 are aligned flushly and light input surfaces 1226 and 1228 are aligned flushly so that the radiation from each of the radiation delivery systems enters the light input surfaces along axes that are substantially parallel to one another.

The radiation delivery systems 1210, 1212, 1214, and 1216 may each include a light-emitting subsystem, a controller, a power source and a cooling subsystem as described earlier with reference to FIG. 1. For thermal management of the radiation delivery systems, cooling elements such as cooling fins, ventilation gratings or holes, and/or fans may be included with the radiation delivery systems. For example, the radiation delivery system 1210 may include ventilation slits 1220 on a top surface and/or a bottom surface (hidden in this perspective view) of the radiation delivery system 1210 and may further include ventilation holes 1222. Similar slits and ventilation holes may be included in each of the radiation delivery systems 1212, 1214, and 1216.

The cabinet 1200 may further include multiple trays or light guides. For illustrative purposes, two trays 1202 and 1204 are shown in FIG. 12A. Tray 1202 includes recessed cutouts 1206 within which workpieces may be positioned as described earlier. Similarly, tray 1204 includes recessed cutouts 1208. Three non-limiting cylindrical recessed cutouts are shown in FIG. 12A. However, the cutout geometry may include various geometries discussed earlier. For example, the recessed cutouts may be formed having a partial cylindrical, partial spherical, triangular (e.g., V-grooves), rectangular, or polygonal (e.g., faceted grooves) cross section. In some embodiments, the trays may include embedded cutouts as described earlier with reference to FIG. 11.

The trays 1202 and 1204 may be easily removed or slid out from the light guide like a drawer as shown in FIG. 2B. Perspective view illustrated in FIG. 12B shows tray 1204 partially drawn out from the cabinet 1200. When inserted back into the cabinet 1200, the tray 1204 may be aligned along the surfaces 1232 and 1228 of the cabinet 1200 as shown in FIG. 12A. Likewise, tray 1202 may also be removable from the cabinet.

However, when the trays are inserted into the cabinet 1200, the trays may aligned such that the light input surfaces of the trays may be in face-sharing contact with the surfaces of the radiation delivery systems of the cabinet through which radiation exits the systems. Specifically, light input surfaces 1228 and 1232 of tray 1204 in FIG. 12B may be flush with the surfaces 1227 and 1231 respectively of the radiation delivery systems 1214 and 1216, when the tray 1204 is inserted into the cabinet 1200.

Accordingly, when the trays are inserted into the cabinet, they may be positioned in a way that aligns the light input surfaces with the light sources of the radiation delivery systems to aid in directing radiation output from the radiation delivery systems into the light input surfaces of the light guides. In this way, the cabinet 1200 may facilitate coupling of the trays to the radiation delivery systems when the trays are inserted, and also facilitate decoupling of the trays from the radiation delivery systems when the trays are removed. There may be additional safety mechanisms on the cabinet that may not allow the tray to be pulled out or removed when the radiation delivery system is active or in use.

The systems and methods described above also provide for a method of irradiating a work piece, the method comprising forming a cutout recessed from a surface of a light guide, positioning the work piece inside the cutout, irradiating a light input surface of the light guide with UV light, and guiding the UV light from within the light guide through recessed surfaces of the cutout to irradiate the work piece. In a first example of the method, the method may additionally or alternatively include wherein forming the cutout comprises forming a recessed cutout volume greater than a work piece volume. A second example of the method optionally includes the first example, and further includes wherein forming the cutout comprises forming the cutout in a first of two opposing parallel surfaces of the light guide, the two opposing parallel surfaces being different from the light input surface. A third example of the method optionally includes one or more of the first and the second examples, and further includes positioning a first reflective surface facing the first of the two opposing parallel surfaces and reflecting incident UV light at the first UV reflective surface on to the work piece. A fourth example of the method optionally includes one or more of the first through the third examples, and further includes positioning a second reflective surface facing a second of the two opposing parallel surfaces and reflecting incident UV light at the second UV reflective surface on to the work piece. A fifth example of the method optionally includes one or more of the first through the fourth examples, and further includes wherein forming the cutout comprises forming recessed spherical surfaces in the first of the two opposing parallel surfaces. A sixth example of the method optionally includes one or more of the first through the fifth examples, and further includes wherein forming recessed cylindrical surfaces in the first of the two opposing parallel surfaces. A seventh example of the method optionally includes one or more of the first through the sixth examples, and further includes forming a plurality of cutouts in the first of the two opposing parallel surfaces.

The systems and methods described above also provide for a radiation delivery system, the system including a light guide comprising a UV transparent tray with one or more cutouts recessed from a surface of the tray, the one or more cutouts shaped to cradle one or more work pieces, and an array of light emitting elements arranged to direct radiation into a light input surface of the tray, wherein the one or more work pieces are irradiated by radiation transmitted from within the tray through recessed surfaces of the one or more cutouts. In a first example of the radiation delivery system, the system may additionally or alternatively include cutouts wherein each of the one or more cutouts comprises a recessed cutout volume greater than a volume of the one or more work pieces. A second example of the radiation delivery system optionally includes the first example and further includes wherein the one or more cutouts are recessed from a first of two opposing parallel surfaces of the tray, the two opposing parallel surfaces being different from the light input surface. A third example of the radiation delivery system optionally includes one or more of the first and the second examples, and further includes wherein the light guide comprises a plurality of the trays arranged in a stack, wherein the first of the two opposing parallel surfaces of each of the trays is positioned flush with the second of the two opposing parallel surfaces of an adjacent tray in the stack, the light input surfaces of each of the trays are flushly aligned, and the array of light emitting elements is arranged to direct radiation into the light input surfaces of each of the UV transparent trays. A fourth example of the radiation delivery system optionally includes one or more of the first through the third examples, and further includes a first reflective surface positioned adjacent to and facing the first of the two opposing parallel surfaces of a tray at an end of the stack, wherein incident UV light at the first reflective surface is reflected back to the first of the two opposing parallel surfaces of the tray at the end of the stack. A fifth example of the radiation delivery system optionally includes one or more of the first through the fourth examples, and further includes a second reflective surface positioned adjacent to and facing the second of the two opposing parallel surfaces of a tray at another end of the stack, wherein incident UV light at the second reflective surface is reflected back to the second of the two opposing parallel surfaces of the tray at the other end of the stack.

The systems and methods described above also provide for a UV light guide for irradiating one or more work pieces, the UV light guide comprising one or more cutouts recessed from a surface of the UV light guide, the one or more cutouts shaped to cradle the one or more work pieces, wherein recessed surfaces of the one or more cutouts comprise UV transmissive surfaces for transmitting UV light from within the UV light guide on to the one or more work pieces. In a first example of the UV light guide, the light guide may additionally or alternatively include wherein the one or more cutouts comprise a recessed cutout volume greater than a volume of the one or more work pieces. A second example of the UV light guide optionally includes the first example and further includes a light input surface for directing UV light into the UV light guide, and two opposing parallel surfaces different from the light input surface, wherein the one or more cutouts are recessed from a first of the two opposing parallel surfaces. A third example of the UV light guide optionally includes one or more of the first and the second examples, and further includes positioning a first UV reflective surface facing the first of the two opposing parallel surfaces. A fourth example of the UV light guide optionally includes one or more of the first through the third examples, and further includes positioning a second UV reflective surface facing a second of the two opposing parallel surfaces.

In this way, the technical effect of delivering more uniform irradiation to the surfaces of a work piece may be achieved as compared to conventional radiation delivery systems. Furthermore, the energy and time consumed during irradiation of the work piece may be reduced, thereby lowering operating costs. Further still, the radiation delivery system may be more compact, thereby making it more convenient and practical for daily applications.

It will be appreciated that the configurations disclosed herein are exemplary in nature, and that these specific embodiments are not to be considered in a limiting sense, because numerous variations are possible. For example, the above embodiments can be applied to work pieces other than optical fibers, cables, and ribbons. Furthermore, the UV curing devices and systems described above may be integrated with existing manufacturing equipment and are not designed for a specific light source. As described above, any suitable light engine may be used such as a microwave-powered lamp, LED's, LED arrays, and mercury arc lamps. The subject matter of the present disclosure includes all novel and non-obvious combinations and sub combinations of the various configurations, and other features, functions, and/or properties disclosed herein.

Note that the example process flows described herein can be used with various UV curing devices and UV curing system configurations. The process flows described herein may represent one or more of any number of processing strategies such as continuous, batch, semi-batch, and semi-continuous processing, and the like. As such, various acts, operations, or functions illustrated may be performed in the sequence illustrated, in parallel, or in some cases omitted. Likewise, the order of processing is not necessarily called for to achieve the features and advantages of the example embodiments described herein, but is provided for ease of illustration and description. One or more of the illustrated acts or functions may be repeatedly performed depending on the particular strategy being used. It will be appreciated that the configurations and routines disclosed herein are exemplary in nature, and that these specific embodiments are not to be considered in a limiting sense, because numerous variations are possible. The subject matter of the present disclosure includes all novel and non-obvious combinations and sub combinations of the various systems and configurations, and other features, functions, and/or properties disclosed herein.

The following claims particularly point out certain combinations and sub combinations regarded as novel and non-obvious. These claims may refer to "an" element or "a first" element or the equivalent thereof. Such claims are to be understood to include incorporation of one or more such elements, neither requiring nor excluding two or more such elements. Other combinations and sub combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method of irradiating a work piece, comprising:
   forming a cutout recessed from a surface of a rectangular light guide, the cutout extending along a width of the light guide;
   positioning the work piece inside the cutout;
   irradiating two light input surfaces of the light guide with UV light, the two light input surfaces having parallel and opposing surfaces; and
   guiding the UV light from within the light guide through recessed surfaces of the cutout to irradiate the work piece; wherein the light guide includes a pair of reflective surfaces for reducing radiation losses due to transmission of radiation originating within the light guide.

2. The method of claim 1, wherein forming the cutout comprises forming a recessed cutout volume greater than a work piece volume.

3. The method of claim 2, wherein forming the cutout comprises forming the cutout in a first of two opposing parallel surfaces of the light guide, the two opposing parallel surfaces being different from the two light input surfaces of the light guide.

4. The method of claim 3, further comprising positioning a first reflective surface facing the first of the two opposing parallel surfaces and reflecting incident UV light at the first UV reflective surface on to the work piece.

5. The method of claim 4, further comprising positioning a second reflective surface facing a second of the two opposing parallel surfaces and reflecting incident UV light at the second UV reflective surface on to the work piece.

6. The method of claim 5, wherein forming the cutout comprises forming recessed spherical surfaces in the first of the two opposing parallel surfaces.

7. The method of claim 5, wherein forming the cutout comprises forming recessed cylindrical surfaces in the first of the two opposing parallel surfaces.

8. The method of claim 5, further comprising forming a plurality of cutouts in the first of the two opposing parallel surfaces.

9. A radiation delivery system, including:
   a light guide comprising a rectangular UV transparent tray with one or more cutouts recessed from a surface of the tray, the one or more cutouts shaped to cradle one or more work pieces and extending along a width of the UV transparent tray;
   wherein the light guide includes a pair of reflective surfaces for reducing radiation losses due to transmission of radiation originating within the light guide;
   an array of light emitting elements arranged to direct radiation into a first pair of opposing parallel light input surfaces of the tray, wherein the one or more work pieces are irradiated by radiation transmitted from within the tray through recessed surfaces of the one or more cutouts; and
   a controller including computer readable instructions for;
   measuring a radiation characteristic at surfaces of the one or more work pieces; and
   adjusting one or more of a radiation output intensity and an exposure duration of the array of light emitting elements based on the measured radiation characteristic.

10. The radiation delivery system of claim 9, wherein each of the one or more cutouts comprises a recessed cutout volume greater than a volume of the one or more work pieces.

11. The radiation delivery system of claim 10, wherein the one or more cutouts are recessed from a first of two opposing parallel surfaces of the tray, the two opposing parallel surfaces being different from the first pair of opposing parallel light input surfaces of the tray.

12. The radiation delivery system of claim 11, wherein the light guide comprises a plurality of the trays arranged in a stack, wherein:
   the first of the two opposing parallel surfaces of each of the trays is positioned flush with a second of the two opposing parallel surfaces of an adjacent tray in the stack;

the light input surfaces of each of the trays are flushly aligned; and the array of light emitting elements is arranged to direct radiation into the light input surfaces of each of the UV transparent trays.

13. The radiation delivery system of claim 12, further comprising a first reflective surface positioned adjacent to and facing the first of the two opposing parallel surfaces of a tray at an end of the stack, wherein incident UV light at the first reflective surface is reflected back to the first of the two opposing parallel surfaces of the tray at the end of the stack.

14. The radiation delivery system of claim 13, further comprising a second reflective surface positioned adjacent to and facing the second of the two opposing parallel surfaces of a tray at another end of the stack, wherein incident UV light at the second reflective surface is reflected back to the second of the two opposing parallel surfaces of the tray at the other end of the stack.

15. A rectangular UV light guide for irradiating one or more work pieces, comprising:

one or more cutouts recessed from a surface of the UV light guide, the one or more cutouts shaped to cradle the one or more work pieces and extending along a width of the UV light guide, wherein recessed surfaces of the one or more cutouts comprise UV transmissive surfaces for transmitting UV light from within the UV light guide on to the one or more work pieces; and wherein the light guide includes a pair of reflective surfaces for reducing radiation losses due to transmission of radiation originating within the light guide.

16. The rectangular UV light guide of claim 15, wherein the one or more cutouts comprise a recessed cutout volume greater than a volume of the one or more work pieces.

17. The rectangular UV light guide of claim 16, further comprising:

a light input surface for directing UV light into the UV light guide, and two opposing parallel surfaces different from the light input surface, wherein the one or more cutouts are recessed from a first of the two opposing parallel surfaces.

18. The rectangular UV light guide of claim 17, further comprising a first UV reflective surface facing the first of the two opposing parallel surfaces.

19. The rectangular UV light guide of claim 18, further comprising a second UV reflective surface facing a second of the two opposing parallel surfaces.

20. The rectangular UV light guide of claim 15, wherein one or more of a width, a depth, and cross-sectional areas of the recessed surfaces are greater than one or more of a width, a depth, and cross-sectional areas of the work pieces.

* * * * *